United States Patent [19]

Kaldor et al.

[11] Patent Number: 5,491,166
[45] Date of Patent: Feb. 13, 1996

[54] INHIBITORS OF HIV PROTEASE USEFUL FOR THE TREATMENT OF AIDS

[75] Inventors: Stephen W. Kaldor; Thomas E. Mabry, both of Indianapolis, Ind.

[73] Assignee: Eli Lilly and Company, Indianapolis, Ind.

[21] Appl. No.: 995,283

[22] Filed: Dec. 22, 1992

[51] Int. Cl.$^6$ ............................ A61K 31/17; A61K 31/27
[52] U.S. Cl. ..................... 514/481; 514/595; 564/165
[58] Field of Search ..................... 544/355; 542/147; 564/165; 514/481, 595

[56] References Cited

U.S. PATENT DOCUMENTS

| | | | |
|---|---|---|---|
| 4,855,286 | 8/1989 | Wagner et al. | 514/19 |
| 5,142,056 | 8/1992 | Kempe et al. | 546/264 |

FOREIGN PATENT DOCUMENTS

| | | |
|---|---|---|
| 52537/90 | 10/1990 | Australia . |
| 0337714 | 10/1989 | European Pat. Off. . |
| 0346847 | 12/1989 | European Pat. Off. . |
| 0361341 | 4/1990 | European Pat. Off. . |
| 0391180 | 10/1990 | European Pat. Off. . |
| 0402646 | 12/1990 | European Pat. Off. . |
| 0432695 | 6/1991 | European Pat. Off. . |
| 0512343 | 11/1992 | European Pat. Off. . |
| 0526009 | 2/1993 | European Pat. Off. . |
| 3627877 | 2/1988 | Germany . |

OTHER PUBLICATIONS

Rich et al., J. Med. Chem., 34(3), 1222–1225 (Mar. 1, 1991).
Huff et al., J. Med. Chem., 34(8), 2305–2314 (Aug. 1, 1991).
Roberts, N. A. et al., Science, 248, 358–361 (1990).
Vara Prasad, J. V. N. et al., Peptides, Chemistry and Biology, Proceedings of the Twelfth American Peptide Symposium, Jun. 16–21, 721–722 (1991).
Thaisrivongs, S. et al., J. Med Chem, 34, 2344–2356 (1991).

*Primary Examiner*—C. Warren Ivy
*Assistant Examiner*—D. Margaret M. Mach
*Attorney, Agent, or Firm*—Janet T. McClain

[57] ABSTRACT

The present invention provides novel HIV protease inhibitors, pharmaceutical formulations containing those compounds and methods of treating and/or preventing HIV infection and/or AIDS.

12 Claims, No Drawings

5,491,166

INHIBITORS OF HIV PROTEASE USEFUL FOR THE TREATMENT OF AIDS

BACKGROUND OF THE INVENTION

A retrovirus designated human immuno-deficiency virus (HIV) is the causative agent of the complex disease termed Acquired Immune Deficiency Syndrome (AIDS), and is a member of the lentivirus family of retroviruses. M. A. Gonda, F. Wong-Staal, R. C. Gallo, "Sequence Homology and Morphological Similarity of HTLV III And Visna Virus, A Pathogenic Lentivirus", Science, 227, 173, (1985); P. Sonigo, N. Alizon, et al., "Nucleotide Sequence of the Visna Lentivirus: Relationship to the AIDS Virus", Cell, 42, 369, (1985). The complex disease AIDS includes progressive destruction of the immune system and degeneration of the central and peripheral nervous systems. The HIV virus was previously known or referred to as LAV, HTLV-III or ARV.

A common feature of retrovirus replication is the post-translational processing of precursor polyproteins by a virally encoded protease to generate mature viral proteins required for viral assembly and function. Interruption of this processing appears to prevent the production of normally infectious virus. Unprocessed structural proteins also have been observed in clones of non-infectious HIV strains isolated from human patients. The results suggest that the inhibition of HIV protease represents a viable method for the treatment of AIDS and the prevention or treatment of infection by HIV.

The HIV genome encodes structural protein precursors known as gag and pol, which are processed to afford the protease, reverse transcriptase and endonuclease/integrase. The protease further cleaves gag and gag-pol polyproteins to yield mature structural proteins of the virus core.

Considerable efforts are being directed toward the control of HIV by means of the structural protein precursors which are processed to yield the retroviral protease, reverse transcriptase and endonuclease/integrase. For example, the currently used therapeutic, AZT, is an inhibitor of the viral reverse transcriptase. H. Mitsuya, NS. Broder, "Inhibition of the In Vitro Infectivity in Cytopathic Effects of HTLV III", Proc. Natl. Acad. Sci. USA, 83, 1911 (1986).

Research efforts have also been directed toward HIV protease inhibitors. For example, European Patent Application (EPA) 361 341; EPA 346 847; EPA 402 646; and EPA 337 714 all disclose compounds which are said to be useful as HIV protease inhibitors.

Unfortunately, many of the known compounds suffer from toxicity problems, lack of bioavailability or short in vivo half-lives. Thus, despite the recognized therapeutic potential associated with a protease inhibitor and the research efforts expended thus far, a viable therapeutic agent has not yet emerged.

Accordingly, a primary object of the present invention is to provide novel HIV protease inhibitors which are useful in the treatment or prevention of both HIV infection and the resulting acquired immune deficiency syndrome (AIDS).

A further object of the present invention is to provide therapeutic compositions that are useful in the treatment or prevention of both HIV infection and AIDS.

Still another object is to provide methods for the treatment or prevention of both HIV infection and the AIDS.

Other objects, features and advantages will become apparent to those skilled in the art from the following description and claims.

SUMMARY OF THE INVENTION

The present invention relates to compounds of formula I, below, and pharmaceutically acceptable salts thereof that inhibit the protease encoded by human immunodeficiency virus (HIV) type 1 (HIV-1) or type 2 (HIV-2). These compounds are useful in the treatment or prevention of HIV infection and the treatment or prevention of the resulting acquired immune deficiency syndrome (AIDS). The compounds, their pharmaceutically acceptable salts, and the pharmaceutical compositions can be used alone or in combination with other antivirals, immunomodulators, antibiotics or vaccines. Methods of treating or preventing AIDS, methods of treating or preventing HIV infection and methods of inhibiting HIV replication are disclosed.

The present invention relates to a method of inhibiting HIV replication in an HIV infected cell, a cell susceptible to HIV infection or a primate in need thereof, thus treating or preventing HIV infection and/or AIDS, comprising administering an effective amount of a compound of formula I

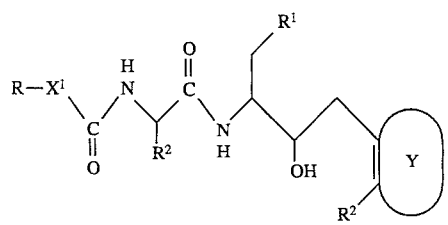

wherein:
R is aryl, heterocycle or unsaturated heterocycle;
$X^1$ is a —$(CH_2)_n$—, —$(CH_2)_m$—O—$(CH_2)_n$— or —$(CH_2)_m$—$NR^0$—$(CH_2)_n$—, where
m and n are independently 0, 1 or 2;
$R^0$ is hydrogen or $C_1$–$C_4$ alkyl;
$R^1$ is aryl, $C_5$–$C_7$ cycloalkyl or —S—$R^{1x}$, where $R^{1x}$ is aryl or $C_5$–$C_7$ cycloalkyl;
$R^2$ is cyano ($C_1$–$C_4$) alkyl, —$CH_2SO_2NH_2$, —$(CH_2)_m$—$X^2$—$R^{2a}$ or —$(CH_2)_m$—$C(O)NR^{2b}R^{2c}$, where
$X^2$ is a bond, —C(O)—O—, —O—, —S—, —S(O)— or —$S(O)_2$—;
$R^{2a}$ is $C_1$–$C_6$ alkyl, aryl, aryl($C_1$–$C_4$)alkyl, heterocycle, heterocycle($C_1$–$C_4$)alkyl, unsaturated heterocycle or unsaturated heterocycle ($C_1$–$C_4$) alkyl;
$R^{2b}$ is hydrogen or $C_1$–$C_4$ alkyl;
$R^{2c}$ is amino, $C_1$–$C_6$ alkoxy, $C_1$–$C_6$ alkyl or —$(CH_2)_z$—di($C_1$–$C_4$)alkylamino;
z is 1,2,3 or 4;
Y is aryl or unsaturated heterocycle;
$R^3$ is a group having the structure:
1) —C(O)—$NR^4R^4$,

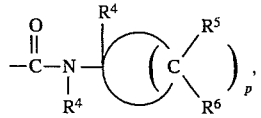

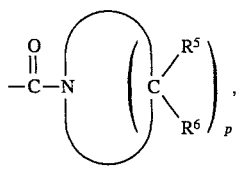

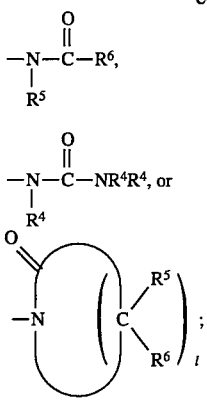

where:

p is 4 or 5;

l is 3, 4 or 5;

$R^4$ at each occurrence is independently hydrogen, $C_1$–$C_6$ alkyl or hydroxy($C_1$–$C_4$)alkyl;

$R^5$ and $R^6$ are independently selected from hydrogen, hydroxy, $C_1$–$C_6$ alkyl, $C_1$–$C_6$ alkoxy, amino, $C_1$–$C_4$ alkylamino, hydroxy ($C_1$–$C_4$) alkyl, carboxy, $C_1$–$C_4$ alkoxycarbonyl, carbamoyl, N—($C_1$–$C_4$) alkylcarbamoyl, aryl, heterocycle or unsaturated heterocycle; or a pharmaceutically acceptable salt thereof.

The present invention also relates to a compound of formula I, or a pharmaceutically acceptable salt thereof, wherein R, $R^1$, $R^2$, $R^3$, $X^1$ and Y are as defined above.

The present invention further provides pharmaceutical formulations comprising a compound of the present invention, or a pharmaceutically acceptable salt thereof, in combination with a pharmaceutically acceptable carrier, diluent or excipient therefor.

DETAILED DESCRIPTION OF THE INVENTION

The present invention provides new compounds of formula I, as described above, that are useful for treating or preventing HIV infection and/or AIDS.

All temperatures stated herein are in degrees Celsius (° C). All units of measurement employed herein are in weight units except for liquids which are in volume units.

As used herein, the term "$C_1$–$C_6$ alkyl" represents a straight or branched alkyl chain having from one to six carbon atoms. Typical $C_1$–$C_6$ alkyl groups include methyl, ethyl, propyl, isopropyl, butyl, isobutyl, sec-butyl, t-butyl, pentyl, neo-pentyl, hexyl and the like. The term "$C_1$–$C_6$ alkyl" includes within its definition the term "$C_1$–$C_4$ alkyl".

"Halo" represents chloro, fluoro, bromo or iodo.

"Halo($C_1$–$C_4$)alkyl" represents a straight or branched alkyl chain having from one to four carbon atoms with 1–3 halogen atoms attached to it. Typical halo($C_1$–$C_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like.

"Cyano($C_1$–$C_4$)alkyl" represents a straight or branched alkyl chain having from one to four carbon atoms with an cyano group attached to it. Typical cyano($C_1$–$C_4$)alkyl groups include cyanomethyl, 2-cyanoethyl, 3-cyanopropyl, 3-cyanopropyl, 2-cyanoisopropyl, 4-cyanobutyl and the like.

"$C_1$–$C_4$ alkylthio" represents a straight or branched alkyl chain having from one to four carbon atoms attached to a sulfur atom. Typical $C_1$–$C_4$ alkylthio groups include methylthio, ethylthio, propylthio, isopropylthio, butylthio and the like.

"$C_1$–$C_4$ alkylamino" represents a straight or branched alkylamino chain having from one to four carbon atoms attached to an amino group. Typical $C_1$–$C_4$ alkylamino groups include methylamino, ethylamino, propylamino, isopropylamino, butylamino, sec-butylamino and the like.

"Di($C_1$–$C_4$)alkylamino" represents a straight or branched dialkylamino chain having two alkyl chains of from one to four carbon atoms attached to a common amino group. Typical di($C_1$–$C_4$)alkylamino groups include dimethylamino, ethylmethylamino, methylisopropylamino, t-butylisopropylamino, di-t-butylamino and the like.

"$C_1$–$C_4$ alkoxy" represents a straight or branched alkyl chain having from one to four carbon atoms attached to an oxygen atom. Typical $C_1$–$C_4$ alkoxy groups include methoxy, ethoxy, propoxy, isopropoxy, butoxy and the like.

"$C_1$–$C_4$ alkoxycarbonyl" represents a straight or branched alkoxy chain having from one to four carbon atoms attached to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl, t-butoxycarbonyl and the like.

"Carbamoyl($C_1$–$C_4$)alkyl" represents a straight or branched alkyl chain having from one to four carbon atoms with a carbamoyl group attached to it. Typical carbamoyl($C_1$–$C_4$)alkyl groups include carbamoylmethyl, carbamoylethyl, carbamoylpropyl, carbamoylisopropyl, carbamoylbutyl and carbamoyl-t-butyl and the like.

"$C_5$–$C_7$ cycloalkyl" represents a saturated hydrocarbon ring structure containing from five to seven carbon atoms which is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, $C_1$–$C_4$ alkylcarbamoyl, amino, $C_1$–$C_4$ alkylamino, di($C_1$–$C_4$)alkylamino or a group having the structure —$(CH_2)_a$—$R^7$ where a is 1, 2, 3 or 4 and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino. Typical cycloalkyl groups include cyclopentyl, cyclohexyl, cycloheptyl, 3-methylcyclopentyl, 4-ethoxycyclohexyl, 5-carboxycycloheptyl, 6-chlorocyclohexyl and the like.

The term "heterocycle" represents an unsubstituted or substituted stable 5- to 7-membered monocyclic or 7-to 10-membered bicyclic heterocyclic ring which is saturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the abovedefined heterocyclic rings is fused to a benzene ring. The heterocyclic ring may be attached at any heteroatom or carbon atom which affords a stable structure. The heterocycle is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, $C_1$–$C_4$ alkylcarbamoyl, amino, $C_1$–$C_4$ alkylamino, di($C_1$–$C_4$)alkylamino or a group having the structure —$(CH_2)_a$—$R^7$ where a is 1, 2, 3 or 4; and $R^7$ is hydroxy, $C_1$–$C_4$ alkoxy, carboxy, $C_1$–$C_4$ alkoxy-carbonyl, amino, carbamoyl, $C_1$–$C_4$ alkylamino or di($C_1$–$C_4$)-alkylamino.

The term "unsaturated heterocycle" represents an unsubstituted or substituted stable 5- to 7-membered monocyclic or 7- to 10-membered bicyclic heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The unsaturated heterocyclic ring may be attached at any heteroatom or carbon atom which affords a stable structure. The unsaturated heterocycle is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, $C_1$–$C_4$ alkylcarbamoyl, amino, $C_1$–$C_4$ alkylamino, di($C_1$–$C_4$)alkylamino or a group having the structure —$(CH_2)_a$—$R^7$ where a is 1, 2, 3 or 4; and $R^7$ is hydroxy, $C_1$–$C_4$ alkoxy, carboxy, $C_1$–$C_4$ alkoxy-carbonyl, amino, carbamoyl, $C_1$–$C_4$ alkylamino or di($C_1$–$C_4$)-alkylamino.

Examples of such heterocycles and unsaturated heterocycles include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl, tetrahydrisoquinolinyl, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8-dimethylnaphthyl, 2-methyl-1,2,3,4-tetrahydroisoquinolinyl, N-methyl-quinolin-2-yl, 2-t-butoxycarbonyl-1,2,3,4-isoquinolin-7-yl and the like.

"Heterocycle ($C_1$–$C_4$)alkyl" represents a straight or branched alkyl chain having from one to four carbon atoms with an heterocycle group attached to it. "Unsaturated heterocycle ($C_1$–$C_4$)alkyl" represents a straight or branched alkyl chain having from one to four carbon atoms with an unsaturated heterocycle group attached to it. Typical heterocycle ($C_1$–$C_4$) alkyl and unsaturated heterocycle ($C_1$–$C_4$) alkyl groups include 3,4,5-trihydrofur-2-ylmethyl, morpholin-2-ylethyl, tetrahydrisoquinolin-3-ylpropyl, pyrrolylmethyl, quinolinylmethyl, 1-indolylethyl, 2-furylethyl, 3-thien-2-ylpropyl, 1-imidazolylisopropyl, 4-thiazolylbutyl and the like.

"Aryl" represents a phenyl or naphthyl ring which is optionally substituted with 1, 2 or 3 substituents independently selected from halo, morpholino ($C_1$–$C_4$)alkyl, pyridyl ($C_1$–$C_4$)alkyl, halo ($C_1$–$C_4$)alkyl, $C_1$–$C_4$ alkyl, $C_1$–$C_4$ alkoxy, carboxy, $C_1$–$C_4$ alkoxycarbonyl, carbamoyl, carbamoyl($C_1$–$C_4$)alkyl, amino, $C_1$–$C_4$ alkylamino, di($C_1$–$C_4$)alkylamino or a group of the formula —$(CH_2)_a$—$R^7$ where a is 1, 2, 3 or 4; and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$) alkylamino. Typical aryl groups include 4-methylphenyl, 3-ethylnaphthyl, 2,5-dimethylphenyl, 8-chloronaphthyl, 3-aminonaphthyl, 4-carboxyphenyl and the like.

"Aryl($C_1$–$C_4$)alkyl" represents a straight or branched alkyl chain having from one to four carbon atoms with an aryl group attached to it. Typical aryl($C_1$–$C_4$) alkyl groups include phenylmethyl, 2-phenylethyl, 3-naphth-1-ylpropyl, 1-naphth-2-ylisopropyl, 4-phenylbutyl and the like.

The term "amino acid side chain" represents the distinctive atom or group bonded to an α-carbon atom also having bonded thereto a carboxyl group and an amino group. These side chains are selected from those found on the following amino acids:

| | |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl and iodoacetyl, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2 - chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-nitrophenylsulfenyl group, the diphenylphosphine oxide group and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group (s). Preferred amino-protecting groups are t-butoxycarbonyl (t-Boc) and benzyloxy-carbonyl (CbZ). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene-dioxybenzyl, benzhydryl, 4,4'-dimethoxybenzhydryl, 2,2',4,4'-tetramethoxy-benzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(dibutylmethylsilyl)ethyl, p-toluenesulfonylethyl, 4-nitrobenzylsulfonylethyl, allyl, cinnamyl, 1-(trimethylsilylmethyl)prop-1-en-3-yl and like moieties. The preferred carboxy-protecting groups are benzhydryl, allyl or benzyl. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds of the present invention have at least three asymmetric centers as denoted by the asterisks in the formula below:

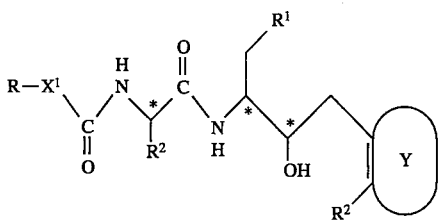

where R, $R^1$, $R^2$, $R^3$, $X^1$ and Y are as defined above in formula I.

As a consequence of these asymmetric centers, the compounds of the present invention can occur as mixtures of diastereomers, racemic mixtures and as individual enantiomers. All asymmetric forms, individual isomers and combinations thereof, are within the scope of the present invention.

As mentioned above, the invention includes the pharmaceutically acceptable salts of the compounds defined by formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonaras, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds of formula I where:

R is aryl or unsaturated heterocycle;

$X^1$ is a —($CH_2$—)$_n$— where n is 0;

$R^1$ is aryl or —S—$R^{1x}$, where $R^{1x}$ is aryl;

$R^2$ is cyano ($C_1$-$C_4$) alkyl, —($CH_2$)$_m$—$X^2$ -$R^{2a}$ or —($CH_2$)$_m$—C(O)N$R^{2b}R^{2c}$, where $X^2$ is —C(O)—O—;

Y is phenyl; and $R^3$ is —C(O)—N$R^4R^4$ or —N($R^5$)C(O)—$R^6$, where $R^4$, $R^5$ and $R^6$ are independently and at each occurrence hydrogen or $C_1$-$C_6$ alkyl; or a pharmaceutically acceptable salt thereof.

Of these preferred compounds, more preferred are those compounds of formula I where:

R is quinolinyl, quinoxalinyl or naphthyl;

$R^1$ is phenyl, phenylthio or naphthylthio;

$R^2$ is cyanomethyl, —$CH_2$—C(O)O-benzyl, —$CH_2$—C(O)OC$H_2$—pyrid—2—yl, —$CH_2$—C(O)NH—methoxy or —$CH_2$—C(O)NH—amino; and $R^3$ is —C(O)—H(t-butyl); or a pharmaceutically acceptable salt thereof.

The most preferred compounds are:

[2R-(2R*, 3S*, 6S*)]-N-t-butyl-2-[2-hydroxy-3-phenylmethyl- 4,7,9-triaza-5,8-dioxo-6-cyanomethyl-10-naphth-1-yl]decyl benzamide;

[2R-(2R*, 3S*, 6S*)]-N-t-butyl-2-[2-hydroxy-3-phenylmethyl- 4,7-diaza-5,8-dioxo -6-cyanomethyl-8-quinolin-2-yl]octyl benzamide;

[2R-(2R*, 3S*, 6S*)]-N-t-butyl-2-[2-hydroxy-3-phenylmethyl- 4,7-diaza-5,8-dioxo-6-cyanomethyl-9-N(methyl)aza-10-quinolin-2-yl]decyl benzamide;

[2R-(2R*, 3S*, 6S*) ]-N-t-butyl-2-[2-hydroxy-3-phenylmethyl- 4-aza-5-oxo-6-N(quinolin-2-ylcarbonyl)amino-7-benzyloxycarbonyl]heptyl benzamide;

[2R-(2R*, 3S*, 6S*)]-N-t-butyl-2-[2-hydroxy-3-phenylmethyl- 4-aza-5-oxo-6-N(quinolin-2-ylcarbonyl)amino-7-(pyrid-2-ylmethoxycarbonyl)]heptyl benzamide;

[2R-(2R*, 3S*, 6R*)]-N-t-butyl-2-[2-hydroxy-3-phenylmethyl- 4-aza-5-oxo-6-N(quinolin-2-ylcarbonyl)amino-7-aminosulfonyl]heptyl benzamide;

[2R-(2R*, 3S*, 6S*)]-N-t-butyl-2-[2-hydroxy-3-phenylmethyl- 4-aza-5-oxo-6-N(quinolin-2-ylcarbonyl)amino-8-N(methoxy)carbamoyl]heptyl benzamide;

[2R-(2R*, 3S*, 6S*)]-N-t-butyl-2-[2-hydroxy-3-phenylmethyl- 4-aza-5,8-dioxo-6-N (quinolin-2-ylcarbonyl)amino-8-hydrazino]octyl benzamide; or a pharmaceutically acceptable salt thereof.

The following list of compounds is provided to further illustrate compounds of formula I included within the scope of the invention:

[2R-(2R*, 3S*, 6S*)]-N-t-butyl-2-[2-hydroxy-3-naphth-2 -ylmethyl-4,7,9-triaza-5,8-dioxo-6-cyanomethyl-10-naphth-1-yl]decyl benzamide;

[2R-(2R*, 3S*, 6S*)]-N-t-butyl-2-[2-hydroxy-3-phenylmethyl- 4,7,9-triaza-5,8-dioxo-6-cyanoethyl-10-naphth-1-yl]decyl benzamide;

[2R-(2R*, 3S*, 6S*)]-N-t-butyl-2-[2-hydroxy-3-phenylthiomethyl- 4,7,9-triaza-5,8-dioxo-6-cyanomethyl-10-naphth-1-yl]decyl benzamide;

[2R-(2R*, 3S*, 6S*)]-N-t-butyt-2-[2-hydroxy-3-naphth-2-ylthiomethyl-4,7,9-triaza-5,8-dioxo-6-cyanomethyl-10-quinolin-2-yl]decyl benzamide;

[2R-(2R*, 3S*, 6S*)]-N-t-butyl-2-[2-hydroxy-3-phenylmethyl- 4,7,9 -triaza-5,8-dioxo-6-cyanobutyl-10-quinolin-2-yl]decyl benzamide;

[2R-(2R*, 3S*, 6S*)]-N-t-butyl-2-[2-hydroxy-3-phenylmethyl- 4,7,9-triaza-5,8-dioxo-6-cyanobutyl-10-benzothien-2-yl]decyl benzamide;

[2R-(2R*, 3S*, 6S*)]-N-t-butyl-2-[2-hydroxy-3-phenylmethyl- 4,7-diaza-5,8-dioxo-6-cyanomethyl-8-naphth-2-yl]octyl benzamide;

[2R-(2R*, 3S*, 6S*)]-N-t-butyl-2-[2-hydroxy-3-phenylmethyl- 4,7-diaza-5,8-dioxo-6-cyanopropyl-8-quinoxalin-2-yl]octyl benzamide;

[2R-(2R*, 3 S*, 6S*)]-N-t-butyl-2-[2 -hydroxy-3-phenylthiomethyl- 4,7-diaza-5,8-dioxo-6-cyanomethyl-8-naphth-2-yl]octyl benzamide;

[2R-(2R*, 3S*, 6S* )]-N-t-butyl-2-[2-hydroxy-3-napth-2-ylthiomethyl-4,7-diaza-5,8-dioxo-6-cyanomethyl-8-naphth-2-yl]octyl benzamide;

[2R-(2R*, 3S*, 6S*)]-N-t-butyl-2-[2-hydroxy-3-phenylthiomethyl- 4,7-diaza-5,8-dioxo-6-cyanomethyl-8-benzothien-2-yl]octyl benzamide;

[2R-(2R *, 3S*, 6S*)]-N-t-butyl-2-[2-hydroxy-3-phenylthiomethyl- 4,7-diaza-5,8-dioxo-6-cyanoethyl-9-N(methyl)aza-10-quinolin-2-yl]decyl benzamide;

[2R-(2R*, 3S*, 6S*)]-N-t-butyl-2-[2-hydroxy-3-phenylmethyl- 4,7 -diaza-5,8-dioxo-6-cyanomethyl-9-aza-10-quinoxalin-2-yl]decyl benzamide;

[2R-(2R*, 3S*, 6S*)]-N-t-butyl-2-[2-hydroxy-3-naphth-2-ylmethyl-4,7-diaza-5,8-dioxo-6-cyanomethyl-9-aza-10-aphth-2-yl]decyl benzamide;

[2R-(2R*, 3S*, 6S*)]-N-t-butyl-2-[2-hydroxy-3-phenylmethyl- 4,7-diaza-5,8-dioxo-6-cyanoethyl-9-N(methyl)aza-10-benzothien-2-yl]decyl benzamide;

[2R-(2R*, 3S*, 6S*)]-N-t-butyl-2-[2-hydroxy-3-phenylmethyl- 4-aza-5-oxo-6-N(naphth-2-ylcarbonyl)amino-7-benzyloxycarbony]heptyl benzamide;

[2R-(2R*, 3S*, 6S*)]-N-t-butyl-2-[2-hydroxy-3-phenylthiomethyl- 4-aza-5-oxo-6-N(naphth-2-ylcarbonyl)amino-7-benzyloxycarbonyl]heptyl benzamide;

[2R-(2R*, 3S*, 6S*)]-N-t-butyl-2-[2-hydroxy-3-naphth-ylthiomethyl- 4-aza-5-oxo-6-N(quinolin-2-ylcarbonyl)amino-7-benzyloxycarbonyl]heptyl benzamide;

[2R-(2R*, 3S*, 6S*)]-N-t-butyl-2-[2-hydroxy-3-phenylmethyl- 4-aza-5-oxo-6-N(phenyl)amino-7-benzyloxycarbony]heptyl benzamide;

[2R-(2R*, 3S*, 6S*)]-N-t-butyl-2-[2-hydroxy-3-phenylmethyl- 4-aza-5-oxo-6-N(pyrid-2-ylmethyl)amino-7-benzyloxycarbonyl]heptyl benzamide;

[2R-(2R*, 3S*, 6S*)]-N-t-butyl-2-[2-hydroxy-3-phenylmethyl- 4-aza-5-oxo-6-N (naphth-2-ylcarbonyl)amino-7-(pyrid-2-ylmethoxycarbonyl)]heptyl benzamide;

[2R-(2R*, 3S*, 6S*)]-N-t-butyl-2-[2-hydroxy-3-phenylthiomethyl- 4-aza-5-oxo-6-N (quinolin-2-ylcarbonyl)amino-7-(pyrid-2-ylmethoxycarbonyl)]heptyl benzamide;

[2R-(2R*, 3S*, 6S*)]-N-t-butyl-2-[2-hydroxy-3-phenylmethyl- 4-aza-5-oxo-6-N(quinolin-2-ylmethyl)amino-7-(pyrid-2-ylmethoxycarbonyl)]heptyl benzamide;

[2R-(2R*, 3S*, 6S*)]-N-t-butyl-2-[2-hydroxy-3-phenylmethyl- 4-aza-5-oxo-6-N(quinolin-2-ylcarbonyl)amino-7-(pyrid-3-ylmethoxycarbonyl)]heptyl benzamide;

[2R-(2R*, 3S*, 6R*)]-N-t-butyl-2-[2-hydroxy-3 -phenylthiomethyl- 4-aza-5-oxo-6-N(quinolin-2-ylcarbonyl)amino-7-aminosulfonyl-]heptyl benzamide;

[2R-(2R*, 3S*, 6R*)]-N-t-butyl-2-[2-hydroxy-3-naphth-2-ylmethyl-4-aza-5-oxo-6-N (quinolin-2-ylcarbonyl)amino-7-aminosulfonyl]heptyl benzamide;

[2R-(2R*, 3S*, 6R*)]-N-t-butyl-2-[2-hydroxy-3-phenylthiomethyl- 4-aza-5-oxo-6-N(pyrid-2-ylcarbonyl)amino -7-aminosulfonyl]heptyl benzamide;

[2R-(2R*, 3S*, 6R*)]-N- t-butyl-2-[2-hydroxy-3-phenylmethyl- 4-aza-5-oxo-6-N(benzyloxycarbonyl)amino-7-aminosulfonyl]heptyl benzamide; or a pharmaceutically acceptable salt thereof.

The compounds of the present invention, or their precursors, can be prepared using procedures known to persons of ordinary skill in art. More particularly, the compounds of formula I maybe prepared according to the procedures shown below in Reaction Scheme I.

Reaction Scheme I:

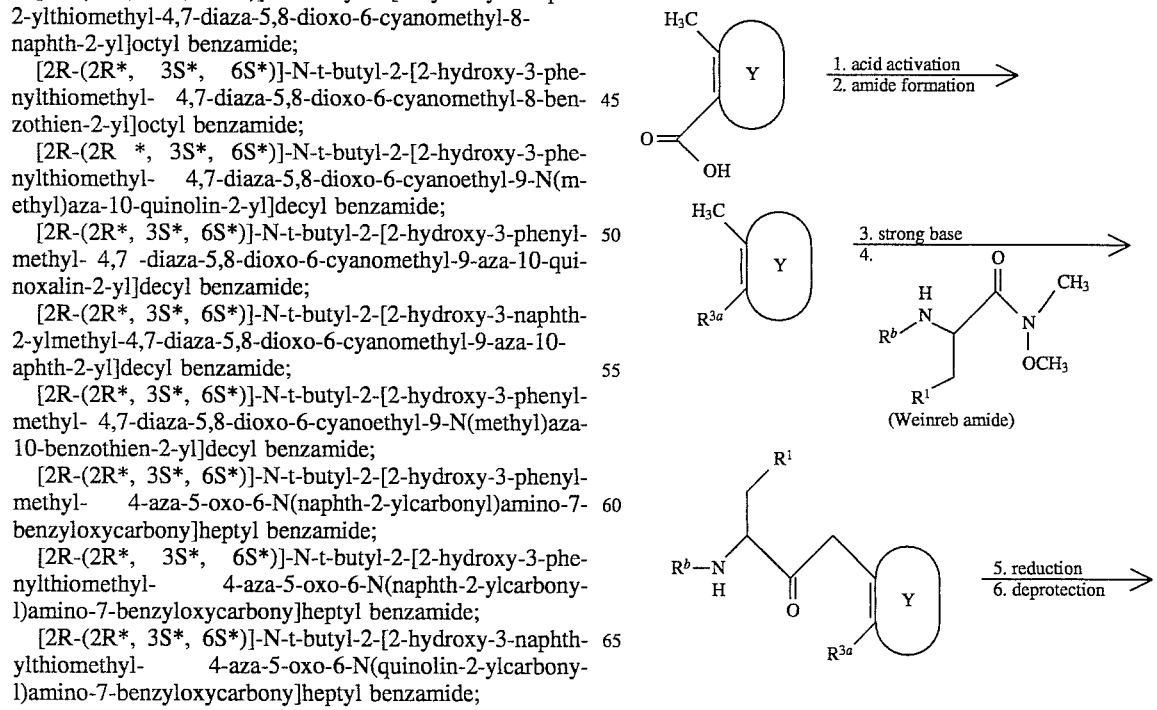

-continued
Reaction Scheme I:

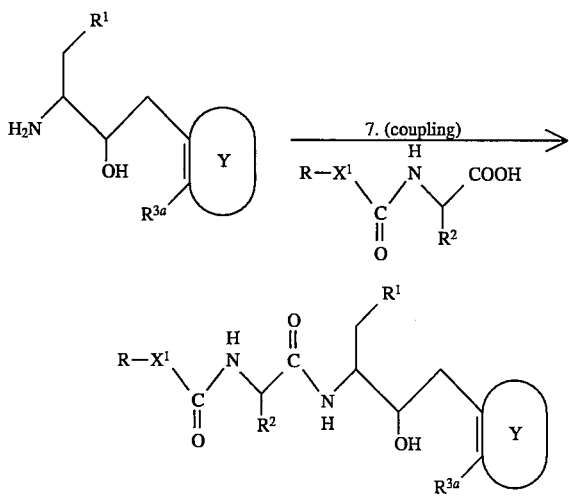

where:

R, $R^1$, $R^2$, $R^{3a}$, $X^1$ and Y are as defined above for formula I; and $R^b$ is an amino-protecting group.

Reaction Scheme I, above, is accomplished by carrying out reactions 1–7 in sequential order. Once a reaction is complete, the intermediate compound may be isolated, if desired, by procedures in the art; for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

In Reaction I.1, the reaction is typically carried out by activating, that is, converting, a suitably substituted aryl, heterocycle or unsaturated heterocycle carboxylic acid to the corresponding acyl chloride or acyl bromide by reaction with thionyl chloride, thionyl bromide, phosphorous trichloride, phosphorous tribromide, phosphorous pentabromide or phosphorous pentachloride according to procedures and under conditions well-known to those skilled in the art. Suitable aryl, heterocycle or unsaturated heterocycle carboxylic acid compounds are commercially available or can be prepared by procedures known in the art.

In Reaction I.2, the acyl chloride or acyl bromide prepared in Reaction I.1 is reacted with ammonia or a primary or secondary amine having the formula

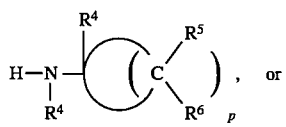

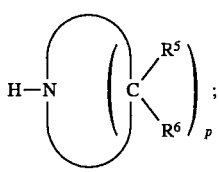

where $R^4$, $R^5$, $R^6$ and p are as defined above for formula I in a nonpolar aprotic solvent or mixture of solvents in the presence or absence of an acid scavenger to afford the corresponding amide. The reaction is carried out at a temperature of from about −20° C. to about 25° C. Typical solvents for this reaction include ethers and chlorinated hydrocarbons, preferably diethyl ether, chloroform or methylene chloride. Preferably, this reaction is carried out in the presence of an acid scavenger such as a tertiary amine, preferably triethylamine.

In Reaction I.3, the amide prepared in Reaction I.2 is reacted with a strong base in the presence of a solubilizing agent to afford the corresponding anion which is then reacted in Reaction I.4 with a Weinreb amide to afford a ketone. Reaction I.3 is carried out in an aprotic solvent at a temperature of from about −78° C. to about 0° C. Typical bases used in Reaction I.3 include lithium amide bases and alkyl lithium bases, preferably $C_1$–$C_4$ alkyllithium bases and lithium di($C_1$–$C_4$)alkylamide bases. Typical solubilizing agents for Reaction I.3 are tetramethyl($C_1$–$C_4$)alkylenediamines, preferably tetramethylethylenediamine. Reaction I.4 is carried out in an aprotic solvent at a temperature from about −80° C. to about −40° C. Typical solvents for Reactions I.3 and I.4 include ethers, preferably tetrahydrofuran. In Reaction I.4, the anion is generally employed in an amount ranging from about equimolar proportions to about a three molar excess of the anion, preferably in about a two molar excess of the anion relative to the Weinreb amide reactant.

In Reaction I.5, the ketone prepared in Reaction I.3 is reduced to the corresponding alcohol using a suitable reducing agent. The reaction is carried out in a protic solvent at a temperature of from about −25° C. to about 25° C. Typical reducing agents for this reaction include sodium borohydride, lithium borohydride, diisobutylaluminum hydride, and sodium bis(2-methoxyethoxy)aluminum hydride. A preferred reducing agent is sodium borohydride. Typical protic solvents for this reaction include alcohols, preferably ethanol.

Reaction I.6 is a standard amino deprotection reaction using procedures and methods well-known to those skilled in the art to afford the corresponding amine.

Reaction I.7 is a standard coupling reaction commonly employed in the synthesis of peptides which is carried out by reacting the amine prepared in Reaction 1.6, with a compound having the formula

R—X—C(O)—NH—CH($R^2$)—COOH where R, X and $R^2$ are as defined above for formula I, in an aprotic solvent or mixture of solvents. The reaction is carried out in the presence or absence of a promoting agent, preferably in the presence of a promoting agent, and in the presence of a coupling reagent. Typical aprotic solvents for this reaction are tetrahydrofuran and dimethylformamide, preferably a mixture of such solvents. The reaction is carried out at a temperature from about −30° C. to about 25° C. The amine reactant is generally employed in equimolar proportions relative to the carboxylic acid reactant, in the presence of an equimolar quantity to a slight excess of the coupling reagent. Typical coupling reagents include the carbodiimides such as dicyclohexylcarbodiimide (DCC) and N,N'-diethylcarbodiimide; the imidazoles such as carbonyldiimidazole; as well as reagents such as bis(2-oxo-3-oxazolidinyl)phosphinic chloride (BOP-Cl) or N-ethoxycarbonyl-2-ethoxy-1,2-dihydroquinoline (EEDQ). A preferred coupling reagent for this reaction is DCC. A promoting agent is preferably included for this reaction; a preferred promoting agent is hydroxybenzotriazole hydrate (HOBT·$H_2O$).

The compounds of formula I can also be prepared according to the procedures shown below in Reaction Scheme II.

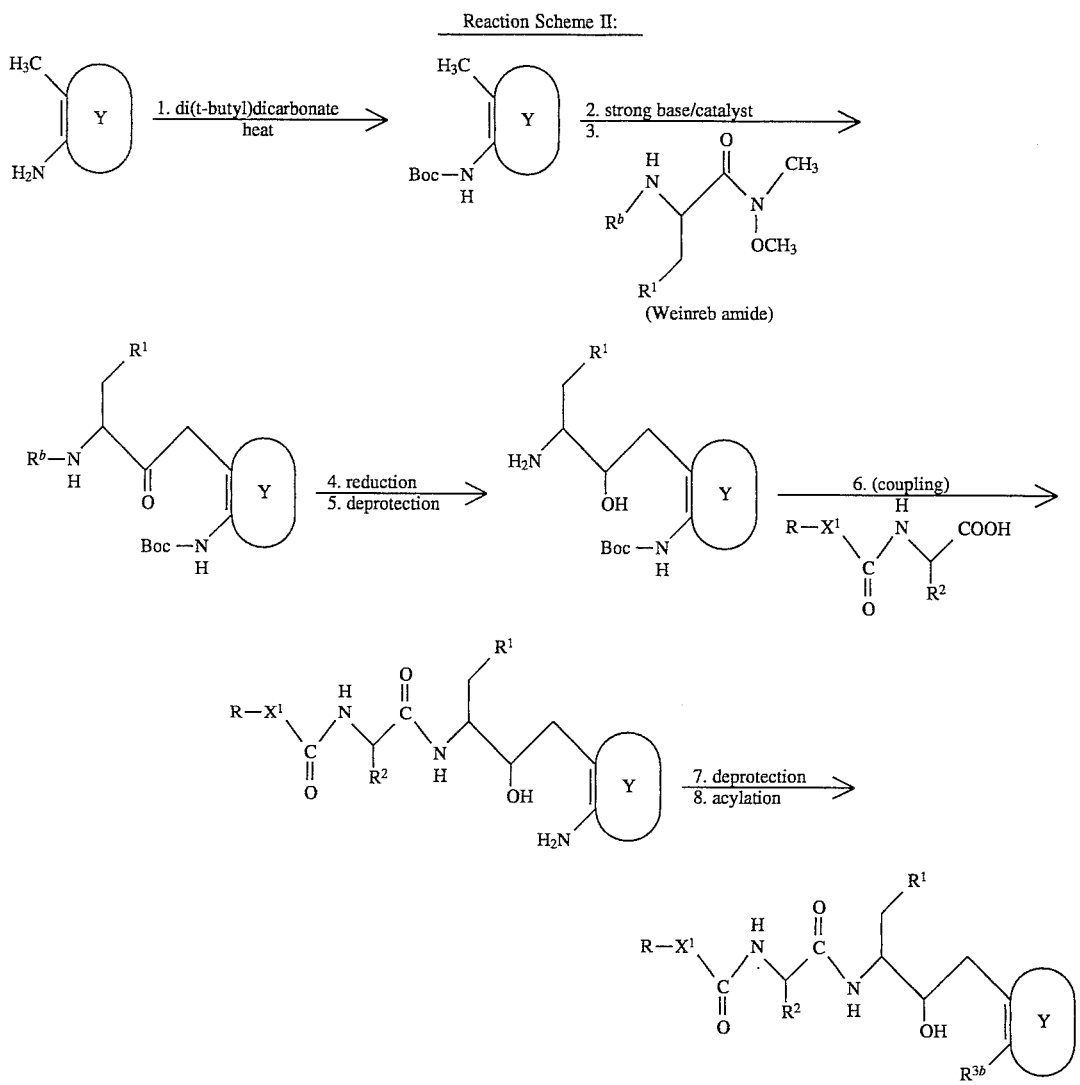

Reaction Scheme II:

where R, $R^1$, $R^2$, $R^{3b}$, Rb, $X^1$ and Y are as defined above.

Reaction Scheme II, is accomplished by carrying out reactions 1–8 in sequential order. Once a reaction is complete, the intermediate compound may be isolated, if desired, by procedures known in the art; for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

In Reaction II.1, a suitably substituted aryl, heterocycle or unsaturated heterocycle amine is protected, under standard conditions used with amino-protecting groups known in the art. Reactions II.2–II.6 are carried out substantially as described above in Reaction Scheme I.3–I.7, with the exception that, in Reaction Scheme II, an additional deprotection reaction, Reaction II.7, is necessary to remove the amino-protecting group introduced in Reaction II.1. This is a standard amino deprotection reaction using procedures and methods known in the art. For example, the t-Boc group illustrated in Reaction Scheme II.1 may be removed using a strong acid, preferably trifluoroacetic acid.

In Reaction II.8, the illustrated intermediate is acylated with a suitable acyl halide, isocyanate or chloroformate, preferably in the presence of an acid scavenger such as a tertiary amine, preferably triethylamine. The reaction is carried out at a temperature of from about −20° C. to about 25° C. Typical solvents for this reaction include ethers and chlorinated hydrocarbons, preferably diethylether, chloroform or methylene chloride.

The Weinreb amide used as a reactant in Reaction I.4 and II.3 is prepared by reacting an amino-protected amino acid with N-methoxy-N-methyl-amine in the presence of a promoting agent, an acid scavenger, and a coupling agent. The reaction is carried out in an aprotic solvent or mixture of solvents at a temperature of from about −25° C. to 25° C. A preferred promoting agent for this reaction is HOBT·H$_2$O. A preferred acid scavengers are tertiary alkylamines, preferably triethylamine or N-methylmorpholine. A preferred coupling reagent is ethyldimethylaminopropyl-carbodiimide hydrochloride. The Weinreb amide afforded by this reaction is preferably isolated prior to its use in Reaction Scheme I.4 and II.3.

The Weinreb amide where $R^1$ is a group having the structure —S—$R^{1x}$ can be prepared by reacting amino-protected serine with triphenylphosphine, diethylazodicarboxylate (DEAD) or dimethylazodicarboxylate (DMAD) in an aprotic solvent at a temperature of from about −80° C. to 0° C. to form the corresponding β-lactone compound. Typical solvents that can be used to accomplish this reaction include the ethers, such as tetrahydrofuran. The resulting lactone compound is then opened by reaction with an appropriately substituted thioanion having the structure, —S—R¹ to provide a carboxylic acid compound of the formula:

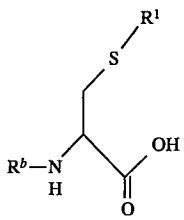

where $R^1$ and $R^b$ are as defined above.

The thioanion compound is preferably formed by reacting the corresponding thiol with a strong base, such as sodium hydride or potassium hydride. The reaction is typically carried out in an aprotic solvent at a temperature from about 0° C. to about 40° C. and under an inert atmosphere, such as nitrogen. Typical solvents for this reaction include ethers, preferably tetrahydrofuran. The resulting carboxylic acid compound is then reacted with N-methoxy-N-methyl-amine in the presence of a promoting agent, an acid scavenger, and a coupling agent and preferably in the presence of an emulsifier in an aprotic solvent or mixture of solvents at a temperature of from about −25° C. to 25° C. A preferred promoting agent for this reaction is HOBT·H₂O. A preferred acid scavengers are tertiary alkylamines, preferably triethylamine or N-methylmorpholine. A preferred coupling reagent is ethyldimethylaminopropylcarbodiimide hydrochloride. The Weinreb amide afforded by this reaction is preferably isolated prior to its use in Reactions I.4 and II.3.

The carboxylic acid reactants used in the coupling reaction described in Reaction Scheme I.7 and II.6, to the extent not commercially available, are prepared using procedures known to those of ordinary skill in the art.

Alternatively, compounds of formula I can be obtained by coupling a compound having the structure

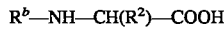

$R^b$—NH—CH($R^2$)—COOH where $R^2$ and $R^b$ are as defined above, with the compound isolated from Reaction I.6, substantially according to the procedure detailed above in Reaction I.7, followed by a deprotection reaction and then either an acylation or another coupling reaction with a compound having the structure R—X¹—COOH, where R and X¹ are as defined above in formula I. This second coupling reaction is carried out substantially in accordance with the procedure detailed in Reaction I.7.

In addition, compounds of formula I, where $R^2$ is a group having the structure —(CH₂)$_m$—C(O)NR$^{2b}$R$^{2c}$, where m, R$^{2b}$ and R$^{2c}$ are as defined above, can also be prepared by first coupling the amine isolated from Reaction I.6 or II.7 with a compound of the formula,

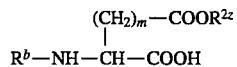

$R^b$—NH—CH—COOH
  |
  (CH₂)$_m$—COOR$^{2z}$ where:
$R^{2z}$ is a carboxy-protecting group; and
$R^b$ and m are as defined above.

The carboxy-protecting group is then removed and the resultant compound is reacted with a suitably substituted amine reactant of the formula H—NR$^{2b}$R$^{2c}$ substantially in accordance with the procedure detailed in Reaction I.7. A preferred solvent for this reaction is a mixture of tetrahydrofuran and dimethylformamide. A preferred coupling reagent for this reaction is DCC. A preferred promoting agent is HOBT·H₂O. The amino-protecting group is then removed from the resultant compound according to procedures and methods known in the art to provide the corresponding amine which may be acylated or sulfonylated according to the procedures discussed above.

The acylation can be carried out with a suitable acyl halide, isocyanate or chloroformate, preferably in the presence of an acid scavenger such as a tertiary amine, preferably triethylamine. The acylation reaction is carried out at a temperature of from about −20° C. to about 25° C. Typical solvents for this reaction include ethers and chlorinated hydrocarbons, preferably diethy lether, chloroform or methylene chloride. The second coupling reaction is carried out substantially in accordance with Reaction I.7.

It will be understood that in performing the processes described above it may be desirable to introduce chemical protecting groups into the reactants in order to prevent secondary reactions from taking place. Any amine, alkylamine or carboxy groups which may be present on the reactants may be protected using any standard amino- or carboxy- protecting group which does not adversely affect the remainder of the molecule's ability to react in the manner desired. Preferred amino-protecting groups are t-Boc and Cbz. Preferred carboxy-protecting groups are benzhydryl, allyl or benzyl. The various protective groups may then be removed simultaneously or successively using methods known in the art.

As noted above, all asymmetric forms, individual isomers and combinations thereof are considered part of this invention. Such isomers may be prepared from their respective precursors by the procedures described above, by resolving the racemic mixtures, or by separating the diastereomers. The resolution can be carried out in the presence of a resolving agent, by chromatography or by repeated crystallization or by some combination of these techniques which are known in the art. Further details regarding resolutions can be found in Jacques et al., Enantiomers, Racemates, and Resolutions, John Wiley & Sons 1981.

The compounds employed as initial starting materials in the synthesis of the compounds of this invention are known and, to the extent not commercially available, can be synthesized by procedures known in the art.

The pharmaceutically acceptable salts of the invention are typically formed by reacting a compound of formula I with an equimolar or excess amount of acid or base. The reactants are generally combined in a mutual solvent, such as diethyl ether or benzene for acid addition salts, or water or alcohols for base addition salts. The salts normally precipitate out of solution within about one hour to about ten days and can be isolated by filtration or other conventional methods.

The following Preparations and Examples further illustrate specific aspects of the present invention. It is to be understood, however, that these examples are included for illustrative purposes only and are not intended to limit the scope of the invention in any respect and should not be so construed.

In the following Preparations and Examples, the terms melting point, nuclear magnetic resonance, electron impact mass spectroscopy, field desorption mass spectroscopy, fast atom bombardment mass spectroscopy spectra, infrared spectroscopy ultraviolet specyroscopy, elemental analysis, high performance liquid chromatography, and thin layer chromatography are abbreviated "m.p.", "NMR", "EIMS", "MS (FD)", "MS (FAB)", "IR", "UV", "Analysis", "HPLC", and "TLC", respectively. In addition, the absorption maxima listed for the IR spectra are only those of interest and not all of the maxima observed.

In conjunction with the NMR spectra, the following abbreviations are used: "s" is singlet, "d" is doublet, "dd" is doublet of doublets, "t" is triplet, "q" is quartet, "m" is multipier, "dm" is a doublet of multiplets and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

The NMR spectra were obtained on a Brüker Corp. 270 MHz instrument or on a General Electric QE-300 300 MHz instrument. The chemical shifts are expressed in delta ($\delta$) values (parts per million downfield from tetramethylsilane). MS(FD) spectra were taken on a Varian-MAT 731 Spectrometer using carbon dendrite emitters. EIMS spectra were obtained on a CEC 21–110 instrument from Consolidated Electrodynamics Corporation. MS(FAB) spectra were obtained on a VG ZAB-3 Spectrometer. IR spectra were obtained on a Perkin-Elmer 281 instrument. UV spectra were obtained on a Cary 118 instrument. HPLC analyses were obtained using C18 Nova-Pak columns using acetonitrile/0.5% ammoniumdihydrogenphosphate (aqueous) at a flow rate of 1.0 mL/min, monitoring by UV at 254 nm. Retention times are expressed in minutes. TLC was carried out on E. Merck silica gel plates. Melting points are uncorrected.

PREPARATION 1

A. N-t-Butyl-2-methylbenzamide

To a cold (0° C.) solution of 139.2 g (0.9 mol) of o-toluoyl chloride in 1200 mL of methylene chloride at 25° C., under nitrogen, was slowly added 180.0 g (1.8 mol) of triethylamine followed by the dropwise addition of a solution containing 73.14 g (1.0 mol) of t-butylamine in 200 mL of methylene chloride. The resulting reaction mixture was warmed to room temperature and allowed to react for 2.5 hours. The reaction mixture was then diluted with 1800 mL of water. The resulting layers were separated, and the organic layer was washed sequentially with 2N sodium hydroxide, 1.0N hydrochloric acid and brine, dried over magnesium sulfate, filtered and then reduced to dryness under reduced pressure to provide 167.6 g of an off-white solid (mp 77°–78° C.).

Yield: 97%.

$^1$H NHR (CDCl$_3$): $\delta$1.41 (s, 9H), 2.41 (s, 3H), 5.54 (br.s, 1H), 7.13–7.30 (m, 4H).

IR (CHCl$_3$): 3430, 3011, 2971, 2932, 1661, 1510, 1484, 1452, 1393, 1366, 1304, 1216, 876 cm$^{-1}$.

MS (FD): m/e 191 (M$^+$), 191 (100).

Analysis for C$_{12}$H$_{17}$NO:

Calcd: C, 75.35; H, 8.76; N, 7.32;
Found: C, 75.10; H, 9.11; N, 7.20.

B. (S)-N-t-Butyl-2-(3-(N-benzyloxycarbonyl)amino-2-oxo-4-phenylbutyl)benzamide

To a solution of 7.0 g (36.5 mmol) of the subtitled intermediate of Preparation 1A in 200 mL anhydrous tetrahydrofuran, was added 12.1 mL (80.3 mmol) N,N,N',N'-tetramethylethylenediamine (TMEDA) was added via syringe. The resulting solution was cooled to −78° C. and then 55.9 mL of sec-butyllithium was added dropwise via syringe while maintaining the temperature of the reaction under −60° C. The resulting reaction solution was then allowed to stir for approximately 1 hour at −78° C. before the addition of a solution containing 5.00 g (14.6 mmol) of (S)-N-methoxy-N-methyl-2-(N-phenylmethyloxycarbonyl)amino-3-phenylpropanamide in 50 mL of anhydrous tetrahydrofuran was added via cannula while maintaining the reaction temperature below −65° C. The resulting reaction mixture was warmed to −20° C., quenched using 20 mL of saturated ammonium chloride and then diluted with 200 mL of diethylether. The resulting layers were separated and the organic layer was washed sequentially with water, 0.2N sodium hydrogen sulfate and brine, dried over sodium sulfate, filtered and then reduced to dryness under reduced pressure to provide a colorless oil. This oil was purified using flash chromatography (eluent of 25% ethyl acetate in methylene chloride) to provide 6.08 g of a colorless foam.

Yield: 88%.

$[\alpha]_D$ −289.26° (c 0.12, MeOH).

$^1$H NMR (CDCl$_3$) a 1.38 (s, 9H), 2.99 (dd, J=15; 6 Hz, 1H), 3.24 (dd, J=15; 6 Hz, 1H), 3.89 (d, J=18 Hz, 1H), 4.16 (d, J=18 Hz, 1H), 4.72 (dd, J=15, 6 Hz, 1H), 5.00–5.09 (m, 2H), 5.56 (d, J=6 Hz, 1H), 5.93 (br. s, 1H), 7.03–7.40 (m, 14H).

IR (CHCl$_3$): 3431, 3027, 3012, 2973, 1713, 1658, 1511, 1454, 1383, 1366, 1307, 1231, 1046 cm$^{-1}$.

MS (FD): m/e 472 (M$^+$), 218 (100).

Analysis for C$_{29}$H$_{32}$N$_2$O$_4$:

Calcd: C, 73.70; H, 6.82; N, 5.93;
Found: C, 73.41; H, 6.98; N, 5.83.

C. [2R-(2R*,3S*)]-N-t-Butyl-2-(3-(N-benzyloxycarbonyl)amino-2-hydroxy-4-phenylbutyl)benzamide To a solution of 6.96 g (14.7 mmol) of the subtitled intermediate of Preparation 1B in 200 mL absolute ethanol, under nitrogen, was added 2.78 g (73.5 mmol) sodium borohydride. When the reaction was substantially complete, as indicated by thin layer chromatography (TLC), the reaction mixture was diluted with 200 mL of ethyl acetate and quenched by the dropwise addition of 20 mL of saturated ammonium chloride. The resulting layers were separated and the organic layer was washed sequentially with 1N hydrochloric acid, saturated sodium bicarbonate solution and brine, dried over sodium sulfate, filtered and then reduced to dryness under reduced pressure to provide 6.4 g of a colorless oil. This oil was purified using flash chromatography (gradient eluent of 2–10% methylene chloride in ethyl acetate) to provide 5.12 g of the major, desired diastereomer.

Yield: 74%.

$[\alpha]_D$ +10.38° (c 0.10, MeOH).

$^1$H NMR (CDCl$_3$): $\delta$1.40 (s, 9H), 2.79 (dd, J=12; 3 Hz, 1H), 2.90–2.98 (m, 2H), 3.04 (44, J=12, 3 Hz, 1H), 3.70–3.81 (m, 1H), 3.97 (m, 1H), 4.96–5.08 (m, 2H), 5.10 (d, J= 9 Hz, 1H), 5.88 (d, J=6 Hz, 1H), 5.93 (S, 1H), 7.1 3–7.42 (m, 14H).

IR (CHCl$_3$): 3431, 3028, 3012, 2971, 1773, 1643, 1515, 1454, 1367, 1229, 1028 cm$^{-1}$.

MS (FD): m/e 475 (M$^+$), 475 (100).

19

Analysis for $C_{29}H_{34}N_2O_4$:

Calcd: C, 73.39; H, 7.22; N, 5.99;

Found: C, 73.12; H, 7.48; N, 5.62.

D. [2R-(2R*, 3S*)]-N-t-Butyl-2-(3-amino-2-hydroxy-4-phenylbutyl)benzamide

A suspension was prepared containing 41.0 g (120 mmol) of the subtitled intermediate of Preparation 1C and 500 mg of 10% palladium-on-carbon in 150 mL absolute ethanol. This suspension was shaken under 60 psi of gaseous hydrogen in a Parr shaker apparatus. The 10% palladium-on-carbon catalyst was then removed by filtration. The resultant filtrate was reduced to dryness under reduced pressure to provide 31.1 g of the desired subtitled intermediate as a light yellow foam. This foam was used without further purification.

Yield: 96%.

$[\alpha]_D$ +34.68° (c 1.0, MeOH).

$^1$H NMR (CDCl$_3$): 1.46 (s, 9H), 2.71 (dd, j=13.7; 9.5 Hz, 1H), 2.84 (dd, J=13.3; 2.51 Hz, 1H), 2.95–3.06 (m, 2H), 3.23–3.29 (m, 1H), 3.84–3.90 (m, 1H), 6.23 (s, 1H), 7.19–7.37 (m, 12H).

IR (CHCl$_3$): 3440, 3382, 3007, 2970, 2934, 1643, 1516, 1454, 1367, 1213 cm$^{-1}$.

MS (FD): m/e 341 (M$^+$), 341 (100).

PREPARATION 2

1-Naphthalenemethylisocyanate

To a stirred solution of 0,400 g (2.55 mmol) of 1-naphthalenemethylamine and 0.88 mL (6.37 mmol) of triethylamine in 30 mL of toluene was added dropwise to a solution of 0,250 g (8.42 mmol) of triphosgene in 20 mL of toluene at 60° C. When the addition was complete, the reaction was refluxed for approximately 15 hours, cooled to 25° C. and then filtered through celite. The filtrate was then concentrated under reduced pressure to provide 100 mg of a thick oil.

Yield: 21%

PREPARATION 3

2-Methyl-1,2,3,4-tetrahydroisoquinoline-3-carboxylic acid

A solution of 0.364 g (2.07 mmol) of 3-carboxy-1,2,3,4-tetrahydroisoquinoline in 25 mL of formic acid was combined with 2.5 mL of 37% formaldehyde. The resulting mixture was allowed to reflux for approximately 17 hours. After cooling, the mixture was contentrated under reduced pressure to provide a gum. This gum was dissolved in 3.0 mL of water, adjusted to a pH 2 using hydrochloric acid and then purified using ion-exchange chromatography (Dowex 50x-8, 100 mesh cation) to provide 0.21 g of a yellow powder.

Yield: 53%

$^1$H NMR (DMSO-d$_6$): δ2.56 (S, 3H), 3.01 (m, 2H), 3.48 (t, 1H), 3.9 (dd, 2H) 7.05 (m, 1H), 7.13 (m, 3H).

MS (FD): m/e 192 (M$^{+2}$).

PREPARATION 4

A. Benzhydryl 2-amino-3-cyano-propanoate

To a solution of 0.9699 g (8.55 mmol) of 2-amino-3-cyanopropanoic acid in 6.0 mL of water, was added 1.61 g (8.5 mmol) of toluene sulfonic acid at 25° C. The resulting mixture was stirred vigorously for approximately ten minutes. The reaction mixture was triturated with diethylether to provide a solid. This solid was isolated using filtration and washed with cold diethylether to provide 2.59 g of a colorless solid. This solid was then redissolved in 40 mL of a 5:3 mixture of methanol/acetonitrile and treated with 3.3 g (17.0 mmol) of diphenyldiazomethane at 35° C. The resulting reaction mixture was quenched using acetic acid, concentrated under reduced pressure to one-half of the original volume, triturated with diethylether and filtered to provide a solid. This solid was isolated,redissolved in a mixture of ethyl acetate and water and then washed with a saturated sodium bicarbonate solution. The organic and aqueous layers were then separated and the organic layer was dried over sodium sulfate, filtered and reduced to dryness to provide 1.9 g of a slightly colored foam.

Yield: 79%

MS (FD): m/e 281 (M$^{+1}$)

Analysis for $C_{17}H_{16}N_2O_2$:

Calcd: C, 72.84; H, 5.75; N, 9.99;

Found: C, 72.61; H, 5.79; N, 9.93.

B. Benzhydryl 2-isocyanato-3-cyano-propanoate

The desired subtitled compound was prepared substantially in accordance with the procedure detailed in Preparation 2 using 1.0 g (0.678 mmol) of the subtitled compound of Preparation 4A, 0.802 g (0.271 mmol) of triphosgene, 2.35 mL (1.69 mmol) of triethylamine in 200 mL of toluene to provide 1.53 g of a slightly colored oil.

Yield: 73%.

MS (FD): m/e 339 (M$^+$ CH$_3$OH).

C. Benzhydryl 2-Cyanomethyl-3-aza-4-oxo-5-N-methylaza-6-quinolin-2-yl hexanoate To a solution of 1.53 g (0.5 mmol) of the subtitled compound of Preparation 4B in 40 mL of methylene chloride, was added 0.86 g (0.5 mmol) of N-methyl-2-naphthalenemethyamine at 23° C., under nitrogen. The resulting reaction mixture was allowed to react for approximately 17 hours. The reaction mixture was reduced to dryness under reduced pressure to provide a foam. This foam was purified, using chromatography (silica gel, eluent of chloroform) to provide 1.32 g of a yellowish foam.

Yield: 55%

$^1$H NMR (CDCl$_3$): δ3.03 (s, 3H), 3.15 (t, 2H), 4.7 (m, 2H), 4.82 (m, 1H), 6.98 (s, 1H), 7.23–7.4 (m, 10H), 7.54 (t, 1H), 7.7 (t, 1H), 7.82 (d, 1H), 8.07 (d, 1H), 8.15 (d, 1H).

MS (FD): m/e 481 (M$^{+3}$)

Analysis for $C_{29}H_{26}N_4O_3$:

Calcd: C, 72.79; H, 5.48; N, 11.71;

Found: C, 72.51; H, 5.76; N, 11.67.

HPLC: 1: 1 acetonitrile/0.5% ammoniumdihydrogenphosphate; $t_R$=3.34.

D. 2-Cyanomethyl-3-aza-4-oxo-5-N-methylaza-6-quinolin-2-yl hexanoic acid

To a solution of 0.600 g (1.25 mmol) of the subtitled compound of Preparation 4C in 10 mL of methanol, was added 0.06 g of 5% palladium-on-carbon and 0.84 (1.25 mmol) of ammonium formate. The reaction mixture was allowed to react at 60° C. for approximately four hours. The resulting mixture was then filtered through celite before cooling. The filtrate was then concentrated under reduced pressure to provide a foam. This foam was redissolved in a mixture of ethyl acetate and water and washed with a saturated sodium bicarbonate solution. The organic and aqueous layers were then separated and the aqueous layer was acidified to pH 6 using a 2.0M sodium bisulfate solution, and then extracted three times using warm ethyl acetate. These combined organic portions were then dried over sodium sulfate, filtered and then concentrated under reduced pressure to provide 0.374 g of a colorless foam.

Yield: 96%

$^1$H NMR (DMSO-d6): δ2.85 (s, 3H), 2.97 (m, 2H), 4.4 (m, 1H) 4.62 (m, 2H), 7.28 (d, 1H), 7.36 (d, 1H), 7.55 (t, 1H), 7.72 (t, 1H), 7.96 (dd, 2H), 8.31 (d, 1H).

MS (FD): m/e 313 (M$^+$1)

PREPARATION 5

2-t-Butoxycarbonyl-1,2,3,4-tetrahydroisoquinoline-7-carboxylic acid

To a solution of 0.051 g (0.282 mmol) of 1,2,3,4-tetrahydroisoquinoline-7-carboxylic acid in 4 mL of a 1:1 mixture of saturated sodium bicarbonate solution and dioxane, was added with 0.067 g (0.31 mmol) of t-butoxycarbonyl anhydride, at 20° C. The resulting reaction mixture was allowed to react for approximately 17 hours. The reaction mixture was then concentrated under reduced pressure to provide a residue. This residue was diluted with ethyl acetate and acidified to pH 4 using sodium bisulfate. The organic and aqueous layers were then separated, and the organic layer was washed with brine, dried over sodium sulfate, filtered and then concentrated under reduced pressure to provide 0.056 g of a thin, colorless oil.

Yield: 72%

$^1$H NMR (CDCl$_3$): δ1.51 (s, 9H), 2.92 (br.m, 2H), 3.7 (br.m, 2H), 4.65 (s, 2H), 7.24 (d, 1H), 7.91 (m, 3H).

PREPARATION 6

Quinaldic acid pentafluorophenyl ester

To a solution of 15.0 g (86.6 mmol) of quinaldic acid in 200 mL of tetrahydrofuran was added 20.8 g (113 mmol) of pentafluorophenol, in one portion. The resulting reaction mixture was allowed to react at room temperature for approximately two hours during which time a gummy precipitate formed at the bottom of the flask. The gum was isolated by decantation and then dissolved in methylene chloride, diluted with hexane, washed sequentially with 0.1N sodiumhydrogensulfate, 1N potassium carbonate and brine, dried over sodium sulfate, filtered and then concentrated under reduced pressure to provide a pale pink solid. This solid was purified by recrystallization from 30 mL of hot diethylether and 400 mL of hot hexane to provide 21.6 g of the desired titled intermediate as colorless needles.

Yield: 73%.

$^1$H NMR (CDCl$_3$): δ7.73 (t, J=7.5 Hz, 1H), 7.86 (t, J=7.9 Hz, 1H), 7.95 (d, J=8.2 Hz, 1H), 8.29–8.42 (m, 3H).

IR (CHCl$_3$): 3035, 2997, 1763, 1522, 1285, 1068, 998, 842 cm$^{-1}$.

Analysis for $C_{16}H_6NO_2F_5$:

Calcd: C, 56.65; H, 1.78; N, 4.13;

Found: C, 56.66; H, 1.77; N, 4.12.

EXAMPLE 1

A. (S) -2-N(benzyloxycarbonyl) amino-3 -cyano-propanoic acid

To a cold (0° C.) suspension of 0.25 g (2.2 mmol) of (L)-2-amino-3-cyano-propanoic acid in 14 mL of a 1:1 mixture of dioxane and a saturated sodium bicarbonate solution, was added 0.34 mL (0.24 mmol) of benzyloxycarbonyl chloride, under nitrogen. The resulting reaction mixture was allowed to react for approximately 17 hours. The reaction mixture was concentrated under reduced pressure to provide a residue. This residue was rediluted with ethyl acetate and acidified to pH 3.0 using sodium bisulfate. The organic and aqueous layers were then separated and the organic layer was washed with brine, dried over sodium sulfate, filtered and then concentrated under reduced pressure to provide 480 mg of a slightly colored oil.

Yield: 88%

B. [2R-(2R*, 3S*, 6S*)]-N-t-Butyl-2-[2-hydroxy-3-phenylmethyl- 4 -aza-5-oxo-6-N(benzyloxycarbonyl)-7-cyano] heptyl benzamide A solution of 0.569 g (1.75 mmol) of the subtitled intermediate of preparation ID was combined sequentially with 0.248 g (1.83 mmol) of hydroxbenzotriazole hydrate (HOBT·H$_2$O), 0.480 g (1.93 mmol) of the subtitled compound of Example 1A and 0.378 g (1.83 mmol) of dicyclohexylcarbodiimide (DCC), at 0° C. under nitrogen. The resulting reaction mixture was slowly warmed to room temperature and allowed to react for approximately 17 hours. The reaction mixture was filtered and the resulting filtrate was diluted with ethyl acetate, washed sequentially with saturated sodium bicarbonate, sodium bisulfate and brine solutions. The organic and aqueous layers were separated and the organic layer was dried over sodium sulfate, filtered and then concentrated to provide a foam. This foam was purified using chromatography (silica dioxide, eluent of 3% methanol in chloroform) to provide 0.610 g of a colorless foam.

Yield: 55%

$^1$H NMR (CDCl$_3$): δ1.42 (s, 9H), 2.7–3.0 (m, 6H), 3.8 (m, 1H), 4.35 (m, 1H), 5.1 (m, 3H), 5.9 (s, 1H), 6.58 (d, 1H), 7.05–7.22 (m, 14H).

MS (FD): m/e 573 (M$^{+2}$)

Analysis for $C_{33}H_{38}N_4O_5$:

Calcd: C, 69.45; H, 6.71; N, 9.82;

Found: C, 69.34; H, 6.78; N, 9.85.

HPLC: 1: 1 acetonitrile/0.5% ammoniumdihydrogenphosphate; $t_R$=2.47.

C. [2R-(2R*,3S*,6S*)]-N-t-Butyl-2-[2-hydroxy-3-phenylmethyl- 4-aza-5-oxo-6-amino-7-cyano]heptyl benzamide The desired subtitled comound was prepared substantially in accordance with the procedure detailed in Preparation 1D using 0.59 g (1.03 mmol) of the subtitled compound of Example 1B and 0.07 g of 5% palladium-on-carbon in 100 mL of absolute ethanol to provide 0.27 g of a colorless foam.

Yield: 59%

MS (FD): 437(M$^{+1}$)

D. [2R- (2R*, 3S*, 6S*)]-N-t-Butyl-2-[2-hydroxy-3-phenylmethyl- 4,7,9-triaza-5,8-dioxo-6-cyanomethyl-10-naphth-1-yl]decyl benzamide To a solution of 41 mg (0.094 mmol) of the subtitled compound of Example 1C in 2 mL of tetrahydrofuran, was added 18 mg (0.098 mmol) of the titled intermediate from Preparation 2 under nitrogen and the resulting reaction mixture was allowed to react overnight at room temperature. When the reaction was substantially complete, as determined by TLC, the mixture was concentrated under reduced pressure to provide an oil. This oil was isolated using chromatography (eluent of 4% methanol in chloroform) to provide 10 mg of a colorless foam.

Yield: 17%.

$^1$H NMR (CDCl$_3$): δ1.46 (s, 9H), 2.7–2.83 (m, 4H), 2.87–3.06 (m, 2H), 3.78 (m, 1H), 4.3 (m, 1H), 4.64 (m, 1H), 4.7 (br. s, 2H), 5.32 (br. s, 1H), 5.99 (br. s, 1H), 7.0–7.4 (m, 16H), 7.5 (m, 2H), 7.78 (br. s, 1H), 7.82 (br. d, 1H), 7.95 (br.d, 1H)MS

MS(FD): m/e 621 (M$^{+2}$).

HPLC: 1:1 acetonitrile/0.5% ammoniumdihydrogenphosphate; t$_R$=6.89 min.

EXAMPLE 2

[2R-(2R*, 3S*, 6S*)]-N-t-Butyl-2-[2-hydroxy-3-phenylmethyl- 4,7-diaza-5,8-dioxo-6-cyanomethyl-8-quinolin-2-yl]octyl benzamide To a solution containing 25.7 mg (0.145 mmol) of 2-carboxyquinoline, 57.9 mg (0.13 mmol) of the subtitled compound of Example 1C and 18.7 mg (0.138 mmol) of HOBT·H$_2$O in 3.5 mL of tetrahydrofuran, was added 28.5 mg (0.138 mmol) of DCC, under nitrogen. The resultant reaction mixture was allowed to react overnight at room temperature, resulting in the formation of a precipitate. The precipitate was removed by filtration and the filtrate was concentrated under reduced pressure to provide a residue. This residue was redissolved in ethyl acetate, washed sequentially with saturated sodium bicarbonate, sodiumbisulfate and brine solutions and then concentrated under reduced pressure to provide a foam. This foam was isolated using chromatography (eluent of 5% methanol in chloroform) to provide 51 mg of a colorless foam.

Yield: 63%.

$^1$H NMR (CDCl$_3$): δ1.48 (s, 9H), 2.82–3.13 (m. 6H), 3.46 (m. 1H), 3.82 (m, 1H), 4.39 (m, 1H), 6.06 (s, 1H), 6.86 (m, 1H), 6.99 (m, 2H) 7.01–7.18 (m. 6H), 7.69 (t, 1H), 7.85 (t, 1H), 7.92 (d, 1H), 8.2 (d, 1H), 8.29 (d, 1H), 8.37 (d, 1H) 8.66 (d, 1H).

MS (FD): m/e 594 (M$^{+2}$), 501, 372, 224.

HPLC: 1:1 acetonitrile/0.5% ammoniumdihydrogenphosphate; t$_R$=7.43 min.

EXAMPLE 3

R-(2R*, 3S*, 6S*)-N-t-Butyl-2-[2-hydroxy-3-phenylmethyl- 4,7-diaza-5,8-dioxo-6-cyanomethyl-8-(2-methyl-1,2,3,4-tetrahydroisoquinolin-3-yl]octyl benzamide The desired titled compound was prepared substantially in accordance with the procedure detailed in Example 2, using 41 mg (0.21 mmol) of the subtitled intermediate from Preparation 3, 85 mg (0.20 mmol) of the subtitled compound of Example 1C and 29 mg (0.14 mmol) of HOBT·H$_2$O and 42 mg (0.20 mmol) of DCC in 7.0 mL of dimethylformamide, to provide a foam. This foam was purified using HPLC (eluent of 2% methanol in chloroform) to provide 15 mg of the desired titled compound.

$^1$H NMR (CDCl$_3$): δ1.46 (s, 9H), 2.82 (m, 4H), 2.99 (m. 5H), 3.77 (m, 1H), 4.29 (m, 1H), 4.52 (br. d, 1H), 4.63 (q, 1H), 4.76 (br.d, 1H), 5.97 (d, 1H), 6.11 (s, 1H), 6.84 (m, 1H), 6.93 (m, 2H), 7.08–7.4 (m, 8H) 7.54 (t, 1H), 7.73 (t, 1H), 7.84 (d, 1H), 8.05 (d, 1H), 8.21 (d, 1H).

MS (FD): m/e 612 (M$^{+2}$).

HPLC: 40/60 acetonitrile/0.5% ammoniumdihydrogenphosphate; t$_R$=11.16 min.

EXAMPLE 4

[2R-(2R*, 3S*, 6S*)]-N-t-Butyl-2-[2-hydroxy-3-phenylmethyl- 4,7-diaza-5,8-dioxo-6-cyanomethyl-9-N(methyl)aza-10-quinolin-2-yl]decyl benzamide The desired titled compound was prepared substantially in accordance with the procedure detailed in Example 1B, using 79.3 mg (0.255 mmol) of the subtitled intermediate of Preparation 4D, 86.7 mg (0,255 mmol) of the subtitled compound of Preparation 1D and 37.8 mg (0.28 mmol) of HOBT·H$_2$O and 52.5 mg (0.267 mmol) of DCC in 4 mL of tetrahydrofuran to provide approximately 30 mg of colorless foam. The resulting foam was purified using flash chromatography (eluent of 2% methanol in chloroform) to provide 30 mg of a colorless foam.

Yield: 5%.

$^1$H NMR (CDCl$_3$): δ1.5 (s, 9H), 2.7–3.1 (m, 1H), 3.75 (m, 1H), 4.3 (m, 1H). 4.52 (d, 1H), 4.64 (m, 1H), 4.76 (d, 1H), 5.97 (d, 1H) 6.12 (s, 1H), 6.85 (m, 1H), 6.9 (m, 2H), 7.1–7.4 (m, 9H), 7.55 (t, 1H), 7.73 (t, 1H), 7.84 (d, 1H), 8.05 (d, 1H), 8.21 (d, 1H).

MS (FD): m/e 637 (M$^{+3}$).

HPLC: 1/1 acetonitrile/0.5% ammoniumdihydrogenphosphate; t$_R$=4.18 min.

EXAMPLE 5

[2R-(2R*, 3S*, 6S*)]-N-t-Butyl-2-[2-hydroxy-3-phenylmethyl- 4,7-diaza-5,8-dioxo-6-cyanomethyl-8-(2-t-butoxycarbonyl-1,2,3,4-tetrahydroisoquinolin-7-yl]octyl benzamide The desired titled compound was prepared substantially in accordance with procedure detailed in Example 2 using 0.09 g (0.21 mmol) of the subtitled intermediate of Example 1C, 0,062 g (0.22 mmol) of the subtitled intermediate of Preparation 5, 0,031 g (0.22 mmol) of HOBT·H$_2$O and 0.044 g (0.21 mmol) of DCC in 3.5 mL of tetrahydrofuran to provide a residue. This residue was purified using chromatography (silica gel, eluent of chloroform) to provide 0.017 g of a colorless foam.

Yield: 8.3%.

$^1$H NMR (CDCl$_3$): δ1.49 (s, 9H), 1.51 (s, 9H), 2.8–3.11 (m, 8H), 3.69 (m, 2H), 3.84 (m, 1H), 4.41 (m, 1H), 4.65 (s, 2H), 4.8 (q, 1H), 5.92 (m. 2H), 6.65 (d, 1H), 6.8 (d, 1H), 7.57–7.1 (m, 12H).

MS (FD): m/e 697 (M$^{+2}$).

EXAMPLE 6

[2R-(2R*, 3S*, 6S*)]-N-t-Butyl-2-[2-hydroxy-3-phenylmethyl-4-aza- 5-oxo-6-N(benzyloxycarbonyl)amino-7-benzyloxycarbonyl]heptyl benzamide The desired titled compound was prepared substantially in accordance with the procedure detailed in Example 2, using 0.25 g (0.70 mmol) of 2-N-(benzyloxycarbonyl)amino-3-benzyloxycarbonyl propanoic acid, 0.24 g (0.70 mmol) of the subtitled compound of Preparation 1D and 0.094 g (0.70 retool) of HOBT·H$_2$O and 0.14 g (0.70 mmol) of DCC in 6 mL of a 5:1 tetrahydrofuran/dimethylformamide solution to provide approximately 0.40 g of a white solid. This solid was purified using flash chromatography (eluent of 2.5% methylene chloride in methanol) to provide 70 mg of a white solid (m.p. 56°–58° C.).

Yield: 14%.

¹H NMR (CDCl₃): δ1.50 (s, 9H), 2.65–2.80 (m, 2H), 2.90–3.10 (m, 4H), 3.70 (m, 1H), 4.25 (m, 1H), 4.53 (m, 1H), 5.10 (m, 4H), 5.72 (d, J=8 Hz, 1H), 5.99 (br.s, 1H), 6.67 (d, J=9 Hz, 1H), 7.20–7.40 (m, 19H).

IR (CHCl₃): 3400, 2980, 1740, 1680, 1520 cm⁻¹.

UV (EtOH): 203 nm (E=51,765), 318 nm (E=146).

MS (FD): m/e 680 (M⁺).

Analysis for $C_{40}H_{45}N_3O_7 \cdot H_2O$:

Calcd: C, 68.85; H, 6.79; N, 6.02;

Found: C, 68.61; H, 6.50; N, 5.73.

EXAMPLE 7

A. [2R-(2a*,3S*,6S*)]-N-t-Butyl-2-[2-hydroxy-3-phenylmethyl- 4-aza-5-oxo-6-N(t-butoxycarbonyl)amino-7-benzyloxycarbonyl]heptyl benzamide The desired subtitled compound was prepared substantially in accordance with the procedure detailed in Example 2, using 4.24 g (13.1 mmol) of (S)-2-N-(t-butoxycarbonyl)amino-3-benzyloxycarbonyl propanoic acid, 4.4 g (12.5 mmol) of the subtitled compound of Preparation 1D and 1.77 g (12.5 mmol) of HOBT·H₂O and 2.62 g (12.5 mmol) of DCC in 50 mL of tetrahydrofuran containing a trace of dimethylformamide, to provide a colorless foam. This foam was purified using flash chromatography (eluent of 50% hexane and ethyl acetate) to provide 4.92 g of a colorless foam.

Yield: 61%.

B. [2R-(2R*,3S*,6S*)]-N-t-Butyl-2-[2-hydroxy-3-phenylmethyl- 4-aza-5-oxo-6-amino-7-benzyloxycarbonyl]heptyl benzamide To a cold (0° C.) solution of 0.89 g (1.38 mmol) of the subtitled compound of Example 7A in 50 mL of methylene chloride, was added 10 mL of trifluoroacetic acid. When the reaction was substantially complete, as indicated by TLC, the reaction mixture was concentrated under reduced pressure to provide a residue. This residue was partitioned between dilute ammonium hydroxide and ethyl acetate. The resulting layers were separated and the organic layer was dried over sodium sulfate, filtered and concentrated under reduced pressure to provide a viscous yellow oil. This oil was recrystallized from diethylether to provide 0.62 g of colorless crystals (m.p. 152°–153° C.).

Yield: 82%.

MS (FD): m/e 546 (M⁺).

Analysis for $C_{32}H_{39}N_3O_5$:

Calcd: C, 70.44; H, 7.20; N, 7.70;

Found: C, 70.50; H, 7.35; N, 7.74.

C. [2R-(2R*,3S*,6S*)]-N-t-Butyl-2-[2-hydroxy-3-phenylmethyl- 4-aza-5-oxo-6-N(quinolin-2-ylcarbonyl)amino-7-benzyloxycarbonyl]heptyl benzamide To a solution containing 0.95 g (2.8 mmol) of the titled intermediate of Preparation 6 and 1.5 g (2.8 mmol) of the subtitled compound of Example 7B in 100 mL of a 3:1 dioxane/water mixture, was added 0.46 g (5.5 mmol) of sodium bicarbonate. When the reaction was substantially complete, as indicated by TLC, the reaction mixture was reduced to dryness under reduced pressure to provide a residue. This residue was redissolved in an ethyl acetate/saturated sodium chloride mixture. The resulting layers were separated and the organic layer was dried over sodium sulfate, filtered and then concentrated under reduced pressure to provide 2.35 g of a pale yellow foam. This foam was purified using flash chromatography (eluent of 50% hexane in ethyl acetate) to provide 1.57 g of a colorless foam (m.p. 81°–83° C.).

Yield: 82%.

¹H NMR (CDCl₃): δ1.48 (s, 9H), 2.78–3.12 (m, 6H), 3.71 (m, 1H), 4.30 (m, 1H), 5.05 (m, 1H), 5.16 (s, 2H), 5.98 (s, 1H), 6.76–6.85 (m, 2H), 6.92 (t, J=9 Hz, 2H), 7.17–7.43 (m, 11H), 7.70 (t, J=9 Hz, 1H), 7.85 (t, J=9 Hz, 1H), 7.95 (d, J=9 Hz, 1H), 8.18 (d, J=9 Hz; 1H), 8.27 (d, J=9 Hz, 1H), 8.39 (d, J=9 Hz, 1H); 9.00 (d, J=12 Hz, 1H).

Analysis for $C_{42}H_{42}N_4O_6 \cdot 0.5EtOAc$:

Calcd: C, 70.95; H, 6.49; N, 7.52;

Found: C, 70.71; H, 6.25; N, 7.44.

EXAMPLE 8

A. [2R-(2R*,3S*,6R*)]-N-t-Butyl-2-[2-hydroxy-3-phenylmethyl- 4-aza-5-oxo-6-N-(t-butoxycarbonyl)amino-7-benzyloxycarbonyl]heptyl benzamide The desired subtitled compound was prepared substantially in accordance with the procedure detailed in Example 2, using 0.95 g (2.9 mmol) of 2-N(t-butoxycarbonyl)amino-3-benzyloxycarbonylpropanoic acid, 1.0 g (2.9 mmol) of the subtitled compound of Preparation 1D and 0.40 g (2.9 mmol) of HOBT·H₂O and 0.6 g (2.9 mmol) of DCC, with the exception that the reaction was run in 6 mL of a 5:1 tetrahydrofuran/dimethylformamide solution to provide 1.87 g of a white solid.

Yield: 98%.

B. [2R-(2R*,3S*,6R*)]-N-t-Butyl-2-[2-hydroxy-3-phenylmethyl- 4-aza-5-oxo-6-amino-7-benzyloxycarbonyl] heptyl benzamide To a solution containing 0.30 g (0.46 mmol) of the subtitled compound of Example 8A and 1 mL of triethylsilane in 5 mL of methylene chloride, was added 2 mL of trifluoroacetic acid. When the reaction was substantially complete, as indicated by TLC, the reaction mixture was concentrated under reduced pressure to provide a residue. This residue was redissolved in 20 mL of methanol containing 1 mL of ammonium hydroxide. The resulting reaction mixture was allowed to react for approximately one hour at room temperature before being concentrated under reduced pressure to provide 0.42 g of a white solid. This solid was purified using flash chromatography (eluent of 5% methanol in methylene chloride) to provide 0.17 g of the desired subtitled compound.

Yield: 68%.

¹H NMR (CDCl₃): δ1.46 (s, 9H), 2.56 (dd, J=8,17 Hz, 1H), 2.75–3.00 (m, 4H), 3.06 (dd, J=5,14 Hz, 1H), 3.50 (m, 1H), 3.78 (m, 1H), 4.24 (m, 1H), 5.07 (d, J=3 Hz, 2H), 6.17 (br. s, 1H), 7.13–7.40 (m, 14H), 7.58 (d, J=9 Hz, 1H).

C. [2R-(2R*,3S*,6R*)]-N-t-Butyl-2-[2-hydroxy-3-phenylmethyl- 4-aza-5-oxo-6-N(quinolin-2-ylcarbonyl)amino-7-benzyloxycarbonyl]heptyl benzamide To a solution containing 0.11 g (1 mmol) of the titled intermediate from Preparation 6 and 0.17 g (1 mmol) of the subtitled compound of Example 8B in 15 mL of a 4:1 dioxane/water mixture, was added 52 mg of sodium bicarbonate. When the reaction was substantially complete, as indicated by TLC, the reaction mixture was concentrated under reduced pressure to provide a residue. This residue was redissolved in 200 mL of an ethyl acetate/saturated sodium bicarbonate mixture. The resulting layers were separated and the organic layer was washed with a brine solution, dried over sodium sulfate, filtered and then concentrated under reduced pressure to provide 0.4 g of a colorless oil.

This oil was purified using flash chromatography (gradient eluent of 40–45% hexane in ethyl acetate) to provide 0.21 g of a white solid.

Yield: 95%.

$^1$H NMR (CDCl$_3$): δ1.43 (s, 9H), 2.62 (dd, J=8 Hz, 1H), 2.75–3.14 (m, 5H), 3.76 (m, 1H), 4.30 (m, 1H), 5.00 (m, 1H), 5.12 (s, 2H), 6.10 (s, 2H), 6.95–7.38 (m, 15H), 7.61 (t, J=7 Hz, 1H), 7.74 (t, J=7 Hz, 1H), 7.85 (d, J=8 Hz, 1H), 8.07 (d, J=9 Hz, 1H), 8.19 (d, J=9 Hz, 1H), 8.26 (d, J=9 Hz, 1H), 9.08 (d, J=8 Hz, 1H).

IR (CHCl$_3$): 3012, 1729, 1664, 1518, 1449 cm$^{-1}$.

UV (EtOH): 205 nm (E=62,487); 239 nm (E=42,162); 292 nm (E=4,139); 316 nm (E=3,025).

MS (FD): m/e 701 (M$^+$).

Analysis for C$_{42}$H$_{44}$N$_4$O$_6$19 1.5H$_2$O:

Calcd: C, 69.31; H, 6.51; N, 7.70;
Found: C, 69.63; H, 6.22; N, 7.44.

EXAMPLE 9

[2R- (2R *, 3S*, 6R*)]-N-t-Butyl-2-[2-hydroxy-3-phenylmethyl-4-aza- 5-oxo-6-N(benzyloxycarbonyl)amino-7-benzyloxycarbonyl]heptyl benzamide To a solution containing 0.20 g of the subtitled compound of Example 8B and 102 μL of triethylamine in 4 mL of methylene chloride, was added 51 μL of phenoxyacetyl chloride, under nitrogen. When the reaction was substantially complete, as indicated by TLC, the reaction mixture was poured into 50 mL of cold (0° C.) aqueous 1N hydrochloric acid. The desired titled compound was extracted using methylene chloride and the resulting organic extracts were dried over sodium sulfate, filtered and then reduced to dryness under reduced pressure to provide 0.23 g of a white solid.

Yield: 92%.

MS (FD): m/e 680 (M$^+$).

Analysis for C$_{42}$H$_{44}$N$_4$O$_6$·1.5H$_2$O:

Calcd: C, 70.67; H, 6.67; N, 6.18;
Found: C, 70.46; H, 6.58; N, 6.20.

EXAMPLE 10

A. [2R-(2R*,3S*,6S*)]-N-t-Butyl-2-[2-hydroxy-3-phenylmethyl- 4-aza-5-oxo-6-N (quinolin-2-ylcarbonyl)amino-7-carboxy]heptyl benzamide To a solution of 1.0 g (1.43 mmol) of the subtitled compound of Example 7C in 20 mL of methanol, was added 100 mg of 5% palladium-on-carbon and 0.5 g of ammonium formate. The resulting mixture was allowed to react for approximate 30 minutes at reflux temperature. The palladium-on-carbon catalyst was then removed by filtration through celite and the resulting filtrate was concentrated under reduced pressure to provide an off-white solid. This solid was suspended in water and ethyl acetate. The resulting layers were separated and the organic layer was washed with a saturated brine solution, dried over sodium sulfate, filtered and then concentrated under reduced pressure to provide 0.87 g of a colorless solid. This solid was purified using reverse phase HPLC (eluent of 1:1 acetonitrile and 0.5% aqueous acetic acid) to provide 40 mg of a colorless solid (m.p. 165°–168° C.).

$^1$H NMR (DMSO-d$_6$): δ1.38 (s, 9H), 2.58–3.05 (m, 6H), 3.61 (br.s, 1H), 3.84 (m, 1H), 4.79 (m, 1H), 5.88 (s, 1.H), 6.92 (t, J=8Hz, 1H), 7.02 (t, J=8 Hz, 2H), 7.12–7.37 (m, 6H), 7.75 (t, J=10 Hz, 2H), 7.90 (t, J=10 Hz, 2H), 7.98 (d, J=10 Hz, 2H), 8.08-8.23 (m, 4H), 8.60 (d, J=10 Hz, 1H); 8.89 (d, J=10 Hz, 1H), 12.40 (s, 1H).

Analysis for C$_{35}$H$_{38}$N$_4$O$_6$:

Calcd: C, 68.84; H, 6.27; N, 9.17;
Found: C, 68.61; H, 6.44; N, 9.10.

B. [2R-(2R*,3S*,6S*)]-N-t-Butyl-2-[2-hydroxy-3-phenylmethyl- 4-aza-5-oxo-6-N(quinolin-2-ylcarbonyl)amino-7-(pyrid-2-ylmethoxycarbonyl)]heptyl benzamide To a solution containing 0.20 g (0.33 mmol) of the subtitled compound of Example 10A, 0.044 g (0.33 mmol) HOBT·H$_2$O and 0.067 g (0.33 mmol) of DCC, was added 0.063 mL (0.66 mmol) of pyrid-2-ylcarbinol. The resulting reaction mixture was heated to 60° C. and allowed to react for approximately eight hours. When the reaction was substantially complete, as indicated by TLC, the reaction mixture was filtered and the filtrate was concentrated under reduced pressure to provide a colorless glass. This glass was purified using flash chromatography (eluent of ethyl acetate containing a trace of ammonium hydroxide) to provide 0.10 g of a colorless solid (m.p. 93°–95° C.).

Yield: 43%.

MS (FD): m/e 702 (M$^+$).

Analysis for C$_{41}$H$_{43}$N$_5$O$_6$:

Calcd: C, 70.17; H, 6.18; N, 9.98;
Found: C, 69.97; H, 6.14; N, 9.72.

EXAMPLE 11

[2R-(2R *, 3S*, 6S*)]-N-t-butyl-2-[2-hydroxy-3-phenylmethyl-4-aza- 5-oxo-6-N(t-butoxycarbonyl)amino-7-benzyloxycarbonyl]heptyl benzamide The titled compound was prepared substantially in accordance with the procedure detailed in Example 2 using 1.0 g (0.29 mmol) of the subtitled intermediate of Preparation 1D, 0.95 g (0.29 mmol) of (2R)-2-N(t-butoxycarbonyl)amino-3-benzyloxycarbonyl propanoic acid, 0.40 g (0.29 mmol) of HOBT·H$_2$O and 0.6 mg (0.29 mmol) of DCC to provide 1.90 g of a white solid. This solid was purified using flash chromatography (eluent of 2.5% methanol in methylene chloride) to provide 1.5 g of a white foam.

Yield: 79%.

Analysis for C$_{37}$H$_{47}$N$_3$O$_7$:

Calcd: C, 68.82; H, 7.34; N, 6.54;
Found: C, 68.65; H, 7.20; N, 6.77.

EXAMPLE 12

[2R-(2R*, 3S*, 6S*)]-N-t-Butyl-2-[2-hydroxy-3-phenylmethyl-4-aza- 5-oxo-6-N(quinolin-2-ylcarbonyl)amino-8-N(methoxy)carbamoyl]heptyl benzamide To a solution containing 175 mg (0.287 mmol) of the subtitled compound of Example 10A, 24 mg (0,287 mmol) of methoxyamine hydrochloride, 39 mg {0.289 mmol) of HOBT·H$_2$O and 60 mg (0.291 mmol) of DCC in 15 mL of anhydrous tetrahydrofuran, was added 0.04 mL (0.287 mmol) of triethylamine. The resultant reaction mixture was heated to 60° C., allowed to react overnight under nitrogen and then cooled to 0° C. resulting in the formation of a precipitate. The reaction mixture was filtered and then concentrated under reduced pressure to provide a residue. This residue was redissolved in ethyl acetate, washed sequentially with 1N aqueous hydrochloric acid, saturated sodium bicarbonate and brine solutions, dried over sodium sulfate, filtered and then concentrated under reduced pressure to provide a crude material. This material was purified using flash chromatography (gradient eluent of 3–10% methanol in methylene chloride) to provide 143 mg of the desired titled compound.

Yield: 78%.

$^1$H NMR (DMSO-d$_6$): δ1.36 (s, 9H), 2.61–2.72 (m, 2H), 2.90–3.02 (m, 2H), 3.29 (m, 2H), 3.44 (s, 3H), 3.58–3.64 (m, 1H), 3.84–3.90 (m, 1H), 4.76–4.83 (m, 1H), 5.83 (d, J=5.1 Hz, 1H), 6.93 (t, J=7.1 Hz, 1H), 7.04 (t, J=7.2 Hz, 2H), 7.16 (d, J=7.4 Hz, 2H), 7.25 (t, J=6.4 Hz, 2H), 7.31 (d, J=7.1 Hz, 2H), 7.73 (t, J=7.5 Hz, 1H), 7.89 (t, J=7.5 Hz, 1H), 8.05–8.21 (m, 5H), 8.59 (d, J=8.6 Hz, 1H), 8.84 (d, J=8.1 Hz, 1H), 11.07 (s, 1H).

IR (KBr): 3297, 2969, 16 56, 1522, 1499, 1366, 1221, 1081, 847, 748, 700 cm$^{-1}$.

MS (FD): m/e 640 (M$^+$, 38), 610 (63), 593 (58), 220 (100).

Analysis for C$_{36}$H$_{41}$N$_5$O$_6$:

Calcd: C, 67.59; H, 6.46; N, 10.95;

Found: C, 67.48; H, 6.52; N, 10.76.

EXAMPLE 13

[2R-(2R*, 3S*, 6S*)]-N-t-Butyl-2-[2-hydroxy-3-phenylmethyl- 4-aza-5,8-dioxo-6-N(quinolin-2-ylcarbonyl)amino-8-hydrazino]octyl benzamide To a solution containing 250 mg (0,409 mmol) of the subtitled compound of Example 10A, 56 mg (0,414 mmol) of HOBT·H$_2$O and 0.02 mL (0.412 mmol) of hydrazine hydrate in 15 mL of anhydrous tetrahydrofuran, was added 85 mg (0.412 mmol) of DCC. The resultant reaction mixture was heated to 60° C., allowed to react overnight under nitrogen and then cooled to 0° C. resulting in the formation of a precipitate. The reaction mixture was filtered and the filtrate concentrated under reduced pressure to provide a residue. This residue was purified using flash chromatography (gradient eluent of 3–10% methanol in methylene chloride) to provide 141 mg of a white foam.

Yield: 55%.

$^1$H NMR (DMSO-d$_6$): δ1.35 (s, 9H), 2.53–2.71 (m, 5H), 2.90–3.02 (m, 2H), 3.58–3.65 (m, 1H), 3.83–3.88 (m, 1H), 4.16–4.22 (m, 1H), 4.74–4.78 (m, 1H), 5.81 (d, J=5.3 Hz, 1H), 6.95 (t, J=7.2 Hz, 1H), 7.05 ( t, J=7.3 Hz, 2H), 7.15–7.32 (m, 6H), 7.70–7.75 (m, 1H), 7.86–7.91 (m,. 1H), 8.02 (d, J=9 Hz, 1H), 8.08–8.20 (m, 4H), 8.56 (d, J=8.5 Hz, 1H), 8.89 (d, J=8.3 Hz, 1H), 9.09 (s, 1H).

IR (KBr): 3300, 1657, 1522, 1491, 847, 748, 701 cm$^{-1}$.

MS (FD): m/e 625 (M$^+$, 100).

Analysis for C$_{35}$H$_{40}$N$_6$O$_5$:

Calcd: C, 67.29; H, 6.45; N, 13.45;

Found: C, 67.42; H, 6.49; N, 13.20.

EXAMPLE 14

A. [2R-(2R*,3S*,6R*)]-N-t-Butyl-2-[2-hydroxy-3-phenylmethyl- 4-aza-5-oxo-6-N-(benzyloxycarbonyl)amino-7-aminosulfonyl]heptyl benzamide The subtitled compound was prepared substantially in accordance with the procedure detailed in Example 1A using 0.10 g (0.29 mmol) of the subtitled intermediate of Preparation 1D, 89 mg (0.29 mmol) of (2R)-2-N(benzyloxycarbonyl)amino- 3-aminosulfonylpropanoic acid, 40 mg (0.29 mmol) of HOBT·H$_2$O and 61 mg (0.29 mmol) of DCC to provide 0.11 g of a white solid. This solid was purified using flash chromatography (eluent of 3% methanol in methylene chloride) to provide 70 mg of a white solid.

Yield: 39%.

$^1$H NMR (CDCl$_3$): δ1.45 (s, 9H), 2.70–3.10 (m, 4H), 3.25–3.50 (m, 2H), 3.85 (m, 1H), 4.30 (m, 1H), 4.65 (m, 1H), 5.06 (s, 2H), 5.48 (br. s, 2H), 5.93 (d, J=8 Hz, 1H), 6.18 (br. s, 1H), 7.10-7.40 (m, 16H) .

$^{13}$NMR (CDCl$_3$): 170.83, 168.65, 156.00, 138.24, 137.33, 135.92, 131.13,130.78, 129.40, 128.54, 128.37, 128.24, 128.10, 126.76, 126.58, 126.36, 74.68, 67.37, 56.02, 55.90, 52.44, 51.45, 36.70, 34.84, 28.68.

IR (CHCl$_3$): 3428, 2976, 1720, 1670, 1643, 1517 cm$^{-1}$.

MS (FD): m/e 625 (M$^+$).

Analysis for C$_{32}$H$_{40}$N$_4$O$_7$S:

Calcd: C, 61.52; H, 6.45; N, 8.97;

Found: C, 61.33; H, .6.53; N, 8.79.

B. [2R-(2R*,3S*,6R*)]-N-t-Butyl-2-[2-hydroxy-3-phenylmethyl- 4-aza-5-oxo-6-amino-7-aminosulfonyl]heptyl benzamide To the subtitled compound of Example 14A in 4 mL of acetonitrile, was added 80 μL of trimethylsilyliodide. When the reaction was substantially complete, as indicated by TLC, the reaction mixture was diluted with methylene chloride and then concentrated under reduced pressure to provide a yellow oil. This oil was partitioned between methylene chloride and sodium thiosulfate. The organic and aqueous layers were separated and the organic layer was dried over sodium sulfate, filtered and then concentrated under reduced pressure to provide 20 mg of a residue. This residue was purified using flash chromatography (eluent of 10% methanol in methylene chloride) to provide 20 mg of the desired subtitled compound.

Yield: 36%.

C. [2R-(2R*,3S*,6R*)]-N-t-Butyl-2-[2-hydroxy-3-phenylmethyl- 4-aza-5-oxo-6-N(quinolin-2-ylcarbonyl)amino-7-aminosulfonyl]heptyl benzamide The subtitled compound was prepared substantially in accordance with the procedure detailed in Example 2 using 20 mg (0.041 mmol) of the subtitled compound of Example 14B, 7 mg (0.041 mmol) of 2-carboxyquinoline, 6 mg (0.045 mmol) of HOBT-H$_2$O and 9 mg (0.043 mmol) of DCC to provide 40 mg of crude material. This material was purified using flash chromatography (gradient eluent of 10% methanol in methylene chloride) to provide 25 mg of a white solid.

Yield: 96%.

$^1$H NMR (CDCl$_3$): δ1.43 (s, 9H), 2.78–3.10 (m, 4H), 3.50–3.75 (m, 2H), 3.90 (m, 1H), 4.37 (m, 1H), 5.18 (m, 1H), 5.60 (br. s, 2H), 6.08 (br. s, 1H), 6.83–7.40 (m, 11H), 7.61 (t, J=8 Hz, 1H), 7.78 (t, J=8 Hz, 1H), 7.82 (d, J=8 Hz, 1H), 8.14 (d, J=8 Hz, 2H), 8.21 (d, J=8 Hz, 1H), 8.90 (d, J=8 Hz, 1H).

MS (FD): m/e 646 (M$^+$).

Analysis for C$_{34}$H$_{39}$N$_5$O$_6$S:

Calcd: C, 63.24; H, 6.09; N, 10.84;

Found: C, 63.45; H, 6.04; N, 10.70.

EXAMPLE 15

[2R -(2R*,3S*,6S*)]-N-t-Butyl-2-[2-hydroxy-3-phenylmethyl-4-aza- 5,8-dioxo-6-N(quinolin-2-ylcarbonyl)amino-8-N(2-(N, N-dimethylamino)ethyl)amino]octyl benzamide The desired titled compound was prepared substantially in accordance with the procedure detailed in Example 2, using 0.20 g (0.33 mmol) of the subtitled compound from Example 10A, 0.072 mL (0.66 mmol) of N,N-dimethylenediamine and 0.044 g of HOBT·H$_2$O and 0.067 mg of DCC in 5 mL of tetrahydrofuran, with the exception that the reaction was run at 60° C. The resultant foam was purified using flash chromatography (eluent of 5% methanol in methylene chloride containing a trace of ammonium hydroxide) to provide 0.123 g of a colorless foam (m.p. 105°–108° C.).

Yield: 55%.

MS (FD): m/e 681 (M$^+$).

Analysis for C$_{39}$H$_{48}$N$_6$O$_5$

Calcd: C, 68.80; H, 7.11; N, 12.34;

Found: C, 68.93; H, 7.11; N, 12.17.

As noted above, the compounds of the present invention are useful for inhibiting HIV protease, which is an enzyme associated with viral component production and assembly. An embodiment of the present invention is a method of treating or preventing HIV infection comprising administering to a primate in need thereof an effective amount of a compound of formula I or a pharmaceutically acceptable salt thereof. Another embodiment of the present invention is a method of treating or preventing AIDS comprising administering to a primate in need thereof an effective amount of a compound of formula I or a pharmaceutically acceptable salt thereof. A further embodiment of the present invention is a method of inhibiting HIV replication comprising administering to an HIV infected cell, a cell susceptible to HIV infection or a primate in need thereof, an effective amount of a compound of formula I or a pharmaceutically acceptable salt thereof.

The term "effective amount" as used herein, means an amount of a compound of the present invention which is capable of inhibiting the HIV protease mediated viral component production and assembly. The HIV protease inhibition contemplated by the present method includes both therapeutic and prophylactic treatment, as appropriate. The specific dose of compound administered according to this invention to obtain therapeutic and/or prophylactic effects will, of course, be determined by the particular circumstances surrounding the case, including, for example, the compound administered, the route of administration, the condition being treated and the individual being treated. A typical daily dose will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using well-known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following formulation examples are illustrative only and are not intended to limit the scope of the invention in any way. The term "active ingredient" means a compound according to formula I or a pharmaceutically acceptable salt thereof.

FORMULATION 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

FORMULATION 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

FORMULATION 3

An aerosol solution is prepared containing the following components:

|  | Weight |
|---|---|
| Active ingredient | 0.25 |
| Methanol | 25.75 |
| Propellant 22 | 70.00 |
| (Chlorodifluoromethane) | |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of active ingredient, are made as follows:

| Active ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| Active ingredient | 100 mg |
|---|---|
| Isotonic saline | 1,000 mL |

The solution of the above ingredients generally is administered intravenously to a subject at a rate of 1 mL per minute.

The following experiment (Fluorescence HIV-1 Protease Inhibitor Assay) was carried out to demonstrate the ability of the compounds of the present invention to inhibit HIV protease.

As used herein, the abbreviations are defined as follows:
BSA—bovine serum albumin
BOC—t-butyloxycarbonyl
BrZ—2-bromobenzyloxycarbonyl
2-ClZ—2-chlorobenzyloxycarbonyl
DCC—dicyclohexylcarbodiimide
DIEA—diisopropylethylamine
DTT—dithiothreitol
EDTA—ethylenediaminetetraacetic acid
FITC—fluorescein isothiocarbamyl
HEPES—4-(2-hydroxyethyl)-1-piperazineethanesulfonic acid
MES—4 morpholineethanesulfonic acid
PAM—phenylacetimidomethyl
TAPS—3-[tris(hydroxymethyl)methyl]amino-1-sulfonic acid
TRIS—tris(hydroxymethyl)aminomethane
TOS—p-toluenesulfonyl (tosyl)

I. PREPARATION OF PROTEASE AND GAG FRACTIONS

A. Culture of *E. coli* K12 L507/pHP10D

Lyophils of *E. coli* K12 L507/pHP10D were obtained from the Northern Regional Research Laboratory, Peoria, Ill. 61604, under the accession number NRRL B-1856 (deposited Nov. 14, 1989). The lyophils were decanted into tubes containing 10 mL LB medium (10 g Bacto-tryprone, 5 g Bacto-yeast extract, and 10 g of sodium chloride per liter; the pH was adjusted to 7.5 and incubated at 32° C., overnight).

A small portion of the overnight culture was placed on LB-agar (LB medium with 15 g/L Bacto-agar) plates containing 12.5 µg/mL tetracycline in a manner so as to obtain a single colony isolate of *E. coli* K12 L507/pHP10D. The single colony obtained was inoculated into 10 mL of LB medium containing 12.5 µg/mL tetracycline and incubated overnight at 32° C. with vigorous shaking. The 10 mL overnight culture was inoculated into LB medium containing 12.5 µg/mL tetracycline and incubated at 32° C. with vigorous shaking until the culture reached mid-log phase.

B. Culture of *E. coli* K12 L507/pHGAG

Lyophils of *E. coli* K12 L507/pHGAG were obtained from the NRRL under the accession number NRRL B-18561 (deposited Nov. 14, 1989). A purified colony of *E. coli* K 12 L507/pHGAG was isolated, and used as an inoculum for a culture which was grown to mid-log phase in substantial accordance with the teaching of Step A, above, for *E. Coli* K12 L507/pHP10D.

C. PREPARATION OF PROTEASE FRACTION

A culture of *E. coli* K12 L507/pHP10D was grown to mid-log phase at 32° C. in LB media containing 12.5 µg/ml tetracycline. The cultivation temperature was quickly elevated to 40° C. to induce gene expression, and the cells were allowed to grow for 2.5 hours at this temperature before the culture was quickly chilled on ice. The cells were centrifuged and the cell pellet was resuspended in 20 mL 50 mmol MES buffer (pH 6.0) containing 1 mmol EDTA, 1 mmol DTT, 1 mmol PMSF and 10% glycerol ("Buffer A"). Cells were lysed by sonication using a Fischer Model 300 Dismembrator and a microtip probe. Following centrifugation at 27,000×g, the supernatant was diluted to a total volume of 60 mL with Buffer A and loaded onto a 2.0×19 cm QAE-Sepharose column (1 mL/min, 4° C.), that had been equilibrated in Buffer A. The column was washed isocratically for 180 min and then eluted with a gradient eluent of 0–1.0M sodium chloride in Buffer A over 120 min. Enzymatic activity was measured by HPLC using the synthetic peptide SQNYPIV as described in Margolin et al., *Biochem, Biophys. Res. Commun.*, 167, 554–560 (1990); the production of the p1 peptide (SQNY) was measured.

The active fractions were combined, made 1.2M in ammonium sulfate, and applied to a 2.0×18 cm hexyl agarose column that had been equilibrated in Buffer A containing 1.2M ammonium sulfate. The sample was loaded at a flow rate of 1 mL/min at 4° C., washed with the equilibration buffer for 240 min (1 mL/min) and then eluted using a reverse linear gradient of 1.2–0M ammonium sulfate in Buffer A for 120 min at the same flow rate. The column was then washed isocratically in Buffer A for 120 min.

The active fractions were combined, concentrated to 10 mL using an Amicon stirred cell with a YM-10 membrane and then applied to a MonoS cation exchange column (1.0×10 cm) that had been equilibrated in Buffer A. The sample was loaded at a flow rate of 1 mL/min at 25° C. After washing isocratically for 30 min, the protease was eluted using a linear gradient of 0–0.45M sodium chloride in Buffer A over 40 min.. The column was washed isocratically in Buffer A containing 0.45M sodium chloride for 30 min.

The active fractions were combined and concentrated to 200 µL using an Amicon stirred cell and a YM-10 membrane and then the protease was applied to a Superose 6 size exclusion column equilibrated in Buffer A containing 0.1M sodium chloride. The column was washed isocratically in this buffer at a flow rate of 0.5 ml/min, following which the HIV protease was eluted as a single peak.

QAE-Sepharose, and hexyl agarose were purchased from Sigma Chemical Company. Superose 6 and MonoS were were purchased from Pharmacia. Buffers and reagents were obtained from Sigma.

D. PREPARATION OF GAG FRACTION

In an analogous manner, a culture of *E. coli* K12 507/pHGAG was grown to mid-log phase at 32° C. then shifted to 40° C. for about 4 to 5 hours. The culture was chilled on ice and centrifuged, then the pellet was resuspended in 8 mL lysis buffer containing 5 mg/mL lysozyme. Lysis buffer was comprised of 50 mM Tris-HCl (pH 7.8), 5 mM EDTA, 1 mM DTT, 100 mM NaCl, µg/mL E64 and 2 µg/mL aprotinin. The culture was incubated about 30 to 60 minutes at 4° C., then briefly sonicated in a Branson® Cell Disrupter at 60% power, for three 20 second bursts with chilling between each burst. The culture was then centrifuged at 15,000×g. The supernatant, which contains the unprocessed gag protein, was partially purified by size exclusion chromatography on a Sephadex G-50 column and stored at −20° C. in 50% glycerol and lysis buffer.

II. PREPARATION OF SUBSTRATE: $N^\alpha$-Biotin-Gly-Ser-Gln-Asn-Tyr-Pro-Ile-Val-Gly-Lys($N^\epsilon$-FITC)-OH

A. Preparation of $N^\alpha$-Biotin-Gly-Ser-Gln-Asn-Tyr-Pro-Ile-Val -Gly-Lys-OH The protected peptide-resin $N^\alpha$-Boc-Gly-Ser-Gln-Asn-Tyr(BrZ)-Pro-Ile-Val-Gly-Lys( 2-ClZ)-OCH$_2$-PAM-resin was synthesized on an Advanced Chemtech Model 200 peptide synthesizer at 1.5 mmol scale using the standard double-couple protocol. The amino terminal Boc group was removed with 50% trifluoroacetic acid in methylene chloride and the resulting resin neutralized with 5% di(isopropyl-)ethylamine (DIEA) in methylene chloride. Then, 1.-1 g (4.5 mmol) of biotin in 20 mL of dimethylsulfoxide was added to the peptide resin, followed by 4.5 mmol of dicyclohexylcarbodiimide (DCC) in 9 mL of methylene chloride. The resulting reaction mixture was diluted to 40 mL total volume using 11 mL methylene chipride, and then allowed to react for approximately 5 hours. The reaction solution was concentrated, the resin washed sequentially with dimethyl sulfoxide, dimethylformamide and methylene chloride and then neutralized with 5% DIEA in methylene chloride. This reaction was repeated twice, with the reaction time being extended to 12 hours per reaction. Ninhydrin analysis of the resin indicated complete reaction of the biotin with the glycine amine group. The final peptide resin was washed extensively with dimethylformamide and methylene chloride and dried to provide 4.3 g (98%).

B. DEPROTECTION

The peptide was deprotected and cleaved from the resin using 50 mL of a hydrofluoric acid/m-cresol solution, 0° C., 1 hour. After removal of the hydrofluoric acid by vacuum distillation, the m-cresol was extracted from the reaction mixture using 100 mL diethylether. The peptide was then solubilized in 50% aqueous acetic acid, frozen and lyophilized to provide 2.14 g.

C. PURIFICATION

The crude $N^\alpha$-Biotin-Gly-Ser-Gln-Asn-Tyr-Pro-Ile-Val-Gly-Lys-OH was dissolved in 200 mL of a 5% acetonitrile (aqueous) solution containing 0.1% trifluoroacetic acid and then filtered through a 0.22 micron filter. The resulting solution was applied to a 2.2×25 cm. reverse phase column of octadecyl-silica (Vydac C-18) which had been equilibrated with the same buffer. The peptide was eluted using an 855 minute linear gradient of 7.5 to 25% acetonitrile, at 2 mL/minute, with collection of fractions. These fractions were analyzed using Analytical HPLC was performed on a 4.6×250 mm Vydac C-18 column using similar buffer conditions. The fractions containing the desired material were combined, frozen and lyophilized to provide 1.206 g (62%).

Amino acid analysis of the isolated $N^\alpha$-Biotin-Gly-Ser-Gln-Asn-Tyr-Pro-Ile-Val-Gly-Lys-OH gave the following ratios: Asn 1.1; Ser 0.96; Gln 1.1; Pro 1.1; Gly 2.1; Val 0.80; Ile 0.78; Tyr 1.1; Lys 1.1; in agreement with theory. Fast-atom bombardment mass spectrometry gave a molecular ion mass peak of 1288, in agreement with theory.

D. LABELING

The purified peptide was labeled with a fluorescent marker at the C-terminal end for use in the Pandex assay. $N^\alpha$-Biotin-Gly-Ser-Gln-Asn-Tyr-Pro-Ile-Val-Gly-Lys-OH (1.206 g, 0.936 mmol) was dissolved in 100 mL of 0.1M sodium borate, pH 9.5. Then, a solution of 3 g (7.7 mmol) of fluorescein isothiocyanate in 15 mL dimethyl sulfoxide was added to the reaction mixture in 10 equal portions over two hours. The resulting mixture was allowed to react for one hour after the final addition. The solution was adjusted to pH 3 using 5N HCl, resulting in the formation of a precipitate which was removed by centrifugation.

The peptide solution was then adjusted to pH 7.8 using 5N sodium hydroxide and then diluted to 200 mL total volume by the addition of 0.1M ammonium acetate, pH 7.5. The resulting solution was then filtered through a 0.22 micron filter and loaded onto a 2.2×25 cm column of Vydac C-18 which had been equilibrated with of 5% acetonitrile in 0.1M ammonium acetate (pH 7.5). The peptide was eluted from the column using an 855 minute linear gradient of 5–25% acetonitrile, at 2 mL/minute, with collection of fractions. Analytical HPLC was used to analyze the fractions. The fractions containing the desired product were then combined, frozen and lyophilized to provide 190.2 mg (12%).

Amino acid analysis of the purified peptide gave the following: Asn 1.1; Ser 1.0; Gln 1.1; Pro 1.1; Gly 2.1; Val 0.8; Ile 0.8; Tyr 1.1; Lys 1.0; in agreement with theory. Fast-atom bombardment mass spectrometry gave amolecular ion mass peak of 1678, in agreement with theory.

E. FLUORESCENCE HIV-1 PROTEASE INHIBITOR ASSAY

The following buffers and solutions are used in the Fluorescence HIV-1 Protease Inhibitor Assay:

MES-ALB Buffer:
0.05M 4-morpholineethane sulfonic acid, pH 5.5
0.02M NaCl
0.002M EDTA
0.001M DTT
1.0 mg/mL BSA
TBSA Buffer:
0.02M TRIS
0.15M NaCl
1.0 mg/mL BSA
Avidin Coated Beads Solution:
0.1% solution of Fluoricon Avidin Assay Particles (Avidin conjugated to solid polystyrene beads, 0.6–0.8 microns in diameter in TBSA Buffer Enzyme Solution:
27 IU/mL of purified HIV-1 protease in MES-ALB buffer (1 IU equals the amount of enzyme required to hydrolyze 1 µmole of substrate per minute at 37° C.

To each well of a round bottom, 96-well plate is added 20 µL of the Enzyme Solution followed by 10 µL of the compound to be evaluated in a 20% aqueous dimethylsulfoxide solution. Purified HIV-1 protease was obtained as described above. The resulting solution is incubated for one hour at room temperature and then 20 µL of a solution containing the substrate, $N^\alpha$-Biotin-Gly-Ser-Gln-Asn-Tyr-Pro-Ile-Val-Gly-Lys($N^\epsilon$-FITC)-OH, in MES-ALB buffer (1.5 µl/mL) is added to each well. The solutions are then incubated for 16 hours at room temperature and then each well is diluted with 150 µL of MES-ALB buffer.

To each well of a second round bottom, 96-well Pandex plate is added 25 uL of the Avidin Coated Beads Solution. Then, to each well is added 25 µL of the diluted incubation solutions, prepared above. The solutions are mixed thoroughly and the plates are loaded into a Pandex® machine, washed, evacuated and read. Sample detection was performed by excitation at 485 nm, reading the resulting epifluorescence at 535 nm.

The $IC_{50}$ results obtained in the Fluorescence Assay for the compounds of tile present invention are set forth below in Table 1. All values have been normalized to a positive control which is [1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-2-quinolinyl carboxamide.

TABLE 1

| Inhibitory Activity of Formula I Compounds | |
|---|---|
| Example No. | Fluorescence Assay $IC_{50}$ in ng/mL |
| Control | 1.0 |
| 1 | 0.4 |
| 2 | 1.1 |
| 3 | 54.6 |
| 4 | 1.2 |
| 5 | — |
| 6 | 7.2 |
| 7 | 0.6 |
| 8 | >1000* |
| 9 | >1000* |
| 10 | 1.3 |
| 11 | $IC_8$ = 1000* |
| 12 | 0.5 |
| 13 | 0.7 |
| 14 | 2.7 |
| 15 | 1.9 |

*The concentration of the compound was not increased above the reported concentration.

We claim:
1. A compound of formula I

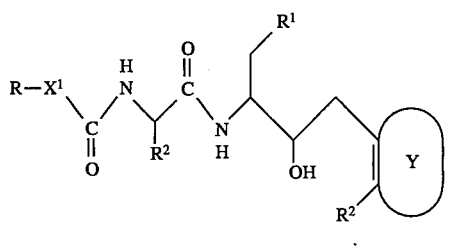

wherein:

R is naphthyl;

$X^1$ is —$(CH_2)_n$—, —$(CH_2)_m$—O—$(CH_2)_n$— or —$(CH_2)_m$—$NR^0$—$(CH_2)_n$—, where m and n are independently 0, 1 or 2;

$R^0$ is hydrogen or $C_1$–$C_4$ alkyl;

$R^1$ is phenyl;

$R^2$ is cyno($C_1$–$C_4$)alkyl

Y is phenyl;

$R^3$ is a group having the structure:

—C(O)—$NR^4R^4$,  1)

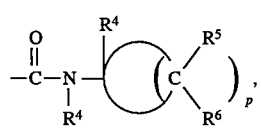  2)

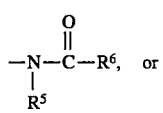  3)

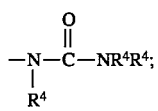  5)

where p is 4 or 5;

$R^4$ at each occurrence is independently hydrogen, $C_1$–$C_6$ alkyl or hydroxy($C_1$–$C_4$)alkyl;

$R^5$ and $R^6$ are independently selected from hydrogen, hydroxy, $C_1$–$C_6$ alkyl, $C_1$–$C_6$ alkoxy, amino, $C_1$–$C_4$ alkylamino, hydroxy($C_1$–$C_4$)alkyl, carboxy, $C_1$–$C_4$ alkoxycarbonyl, carbamoyl, N-($C_1$–$C_4$)alkylcarbamoyl, and aryl; or a pharmaceutically acceptable salt thereof.

2. A compound according to claim 1 wherein:

$X^1$ is —$(CH_2)_n$— where n is 0; and $R^3$ is —C(O)—$NR^4R^4$ or —N($R^5$)C(O)—$R^6$, where $R^4$, $R^5$ and $R^6$ are independently and at each occurrence hydrogen or $C_1$–$C_6$ alkyl; or a pharmaceutically acceptable salt thereof.

3. A compound according to claim 2 wherein:

$R^2$ is cyanomethyl; and $R^3$ is —C(O)—NH(t-butyl); or a pharmaceutically acceptable salt thereof.

4. A compound according to claim 3 which is [2R -(2R *,3 S*,6S*)]-N-t-butyl-2-[2-hydroxy-3-phenylmethyl- 4,7,9-triaza-5,8-dioxo-6-cyanomethyl-10-naphth-1-yl]decyl benzamide; or a pharmaceutically acceptable salt thereof.

5. A pharmaceutical formulation comprising a pharmaceutically acceptable carrier, diluent or excipient and a compound of claim 1.

6. A pharmaceutical formulation according to claim 5 where the compound is one wherein:

$X^1$ is —$(CH_2)_n$— where n is 0; and $R^3$ is —C(O)—$NR^4R^4$ or —N($R^5$)C(O)—$R^6$, where $R^4$, $R^5$ and $R^6$ are independently and at each occurrence hydrogen or $C_1$–$C_6$ alkyl; or a pharmaceutically acceptable salt thereof.

7. A pharmaceutical formulation according to claim 5 where the compound is one wherein:

$R^2$ is cyanomethyl; and $R^3$ is —C(O)—NH(t-butyl); or a pharmaceutically acceptable salt thereof.

8. A pharmaceutical formulation according to claim 7 where the compound is [2R-(2R*,3S*,6S*)]-N-t-butyl-2-[2-hydroxy-3-phenylmethyl-4,7,9-triaza-5,8-dioxo-6-cyanomethyl-10-naphth-1-yl]decyl benzamide; or a pharmaceutically acceptable salt thereof.

9. A method of inhibiting HIV replication comprising administering to an HIV infected cell, or a cell susceptible to HIV infection an effective amount of a compound of claim 1.

10. A method according to claim 9 where the compound is one wherein:

$X^1$ is —$(CH_2)_n$— where n is 0; and $R^3$ is —C(O)—$NR^4R^4$ or —N($R^5$)C(O)—$R^6$, where $R^4$, $R^5$ and $R^6$ are independently and at each occurrence hydrogen or $C_1$–$C_6$ alkyl; or a pharmaceutically acceptable salt thereof.

11. A method according to claim 10 where the compound is one wherein:

$R^2$ is cyanomethyl; and $R^3$ is —C(O)—NH(t-butyl); or a pharmaceutically acceptable salt thereof.

12. A method according to claim 11 where the compound is [2R-(2R*,3S*,6S*)]-N-t-butyl-2-[2-hydroxy-3-phenylmethyl- 4,7,9-triaza-5,8-dioxo-6-cyanomethyl-10-naphth-1-yl]decyl benzamide; or a pharmaceutically acceptable salt thereof.

* * * * *